United States Patent
Tanigawa

(10) Patent No.: US 6,707,876 B2
(45) Date of Patent: Mar. 16, 2004

(54) X-RAY CT APPARATUS AND METHOD

(75) Inventor: Shunichiro Tanigawa, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/151,496

(22) Filed: May 20, 2002

(65) Prior Publication Data

US 2002/0191737 A1 Dec. 19, 2002

(30) Foreign Application Priority Data

May 22, 2001 (JP) ...................................... 2001-151922

(51) Int. Cl.$^7$ ................................................ A61B 6/00
(52) U.S. Cl. ........................................ 378/19; 378/901
(58) Field of Search ................................... 378/19, 901

(56) References Cited

U.S. PATENT DOCUMENTS

| | | | |
|---|---|---|---|
| 4,220,863 A | 9/1980 | McBride et al. | 250/445 T |
| 4,464,776 A | 8/1984 | Erker | 378/10 |
| 5,065,436 A | 11/1991 | Matsumura | 382/6 |
| 5,732,117 A | 3/1998 | Sato et al. | 378/19 |
| 5,949,843 A | 9/1999 | Tamaki et al. | 378/17 |
| 5,974,108 A | 10/1999 | Taguchi et al. | 378/4 |
| 6,028,908 A | 2/2000 | Taguchi | 378/15 |
| 6,157,696 A | 12/2000 | Saito et al. | 378/19 |
| 6,169,779 B1 | 1/2001 | Lai | 378/19 |
| 6,215,843 B1 | 4/2001 | Saito et al. | 378/19 |
| 6,243,438 B1 | 6/2001 | Nahaliel et al. | 378/19 |
| 6,327,331 B1 | 12/2001 | Toth et al. | 378/20 |
| 6,359,957 B1 | 3/2002 | Toth | 378/19 |
| 6,411,671 B2 | 6/2002 | Bruder et al. | 378/4 |
| 6,415,013 B1 | 7/2002 | Hsieh et al. | 378/19 |
| 6,445,764 B2 * | 9/2002 | Gohno et al. | 378/19 |
| 6,567,495 B2 * | 5/2003 | McGrath et al. | 378/19 |

* cited by examiner

Primary Examiner—Craig E. Church
Assistant Examiner—Jurie Yun
(74) Attorney, Agent, or Firm—Carl B. Horton, Esq.; Armstrong Teasdale LLP

(57) ABSTRACT

In order to efficiently obtain projection data having a variety of slice widths (slice patterns) in one scan, an X-ray CT apparatus is provided in which an X-ray tube 40 and an X-ray detector 70 are opposed to each other interposing a subject 100, in which detector a multiplicity of X-ray detector elements are linearly arranged in the channel arrangement direction to form a plurality of rows in the subject body axis direction, for reconstructing a CT tomographic image of the subject based on detected signals from the X-ray detector, wherein the X-ray CT apparatus comprises signal duplicating means 81a for duplicating channel detected signals of the X-ray detector 70 and distributing the duplicated signals to a plurality of groups a, b, etc.; and signal combining means 81b that can combine the distributed duplicated signals in each group in an arbitrary pattern across the detector rows for each channel.

28 Claims, 22 Drawing Sheets

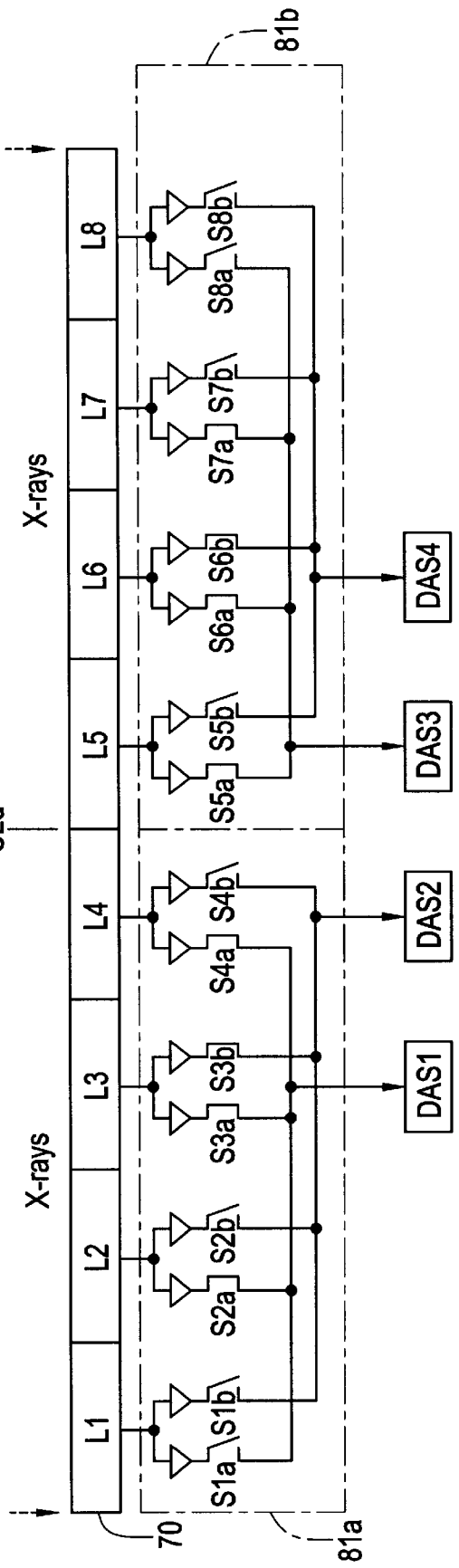

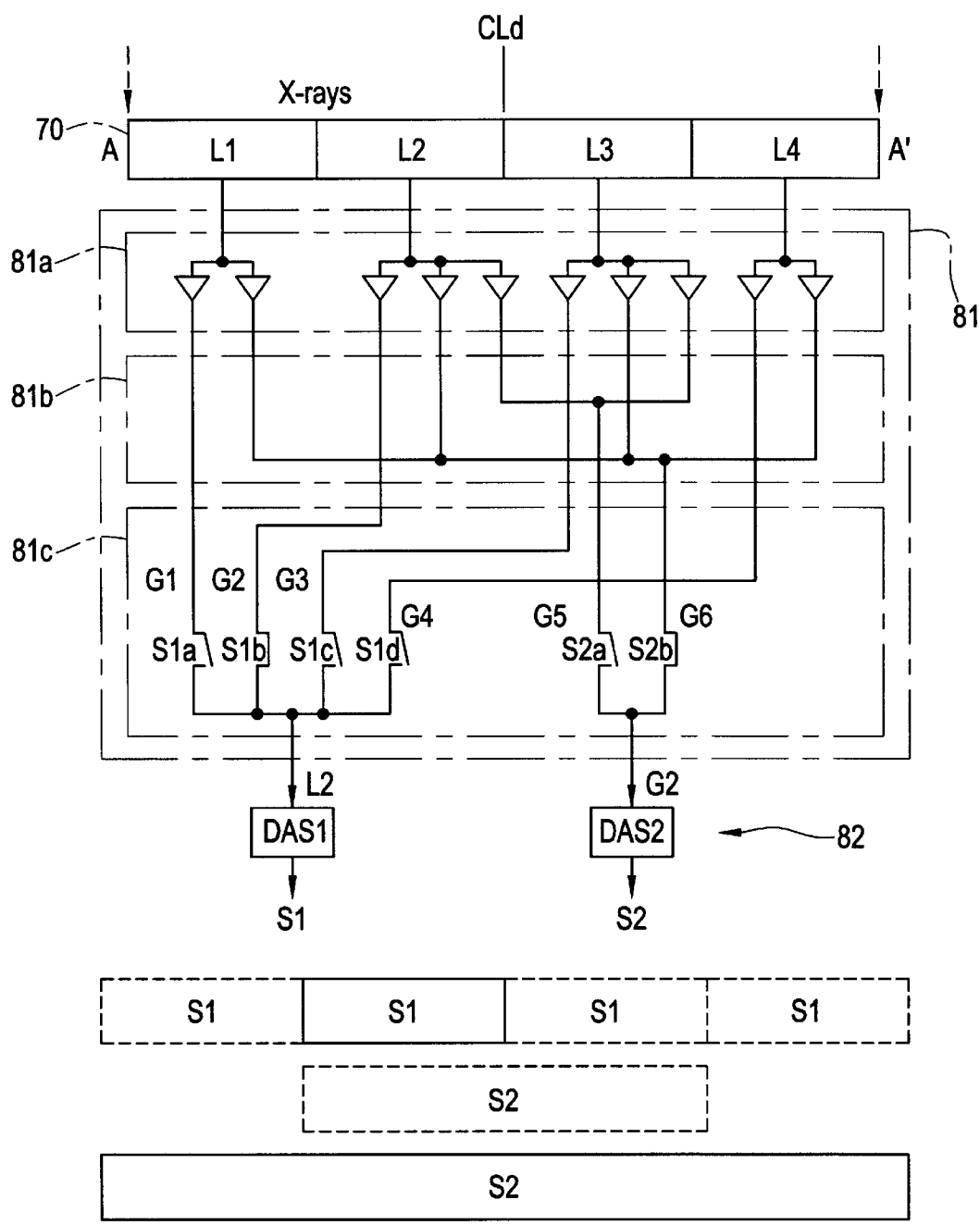

X-RAY CT APPARATUS AND METHOD

CROSS REFERENCE TO RELATED APPLICATIONS

This application claims the benefit of Japanese Application No. 2001-151992 filed May 22, 2001.

BACKGROUND OF THE INVENTION

The present invention relates to an X-ray CT apparatus and method, and more particularly to an X-ray CT apparatus and method in which an X-ray tube and an X-ray detector (multi-row detector) are opposed to each other interposing a subject, which detector comprises a multiplicity of X-ray detector elements linearly arranged in the channel arrangement direction to form a plurality of rows in the subject body axis direction, for reconstructing a CT tomographic image of the subject based on detected signals from the X-ray detector.

In the X-ray CT apparatus of this type, since projection data can be simultaneously obtained from the plurality of rows of the multi-row detector in one scan, the speed of X-ray CT imaging can be increased. However, the apparatus cannot be flexibly adapted to imaging for various medical purposes because the scan (projection) data collecting scheme (i.e., a pattern of slices of the subject) is fixed, and improvement is desired.

FIG. 1 is a configuration diagram of the main portion of a conventional X-ray CT apparatus. The apparatus is generally comprised of a scan gantry section 30 for performing an axial/helical scan and reading on the subject by an X-ray fan beam XLFB, an imaging table 20 for supporting the subject 100 and moving the subject 100 in the body axis CLb direction, and an operating console section 10 remotely located for controlling the scan gantry section 30 and imaging table 20, and being operated by, for example, a radiologist.

In the scan gantry section 30, reference numeral 40 designates a rotary anode type X-ray tube, 150 a collimator for limiting the irradiation width of X-rays in the body axis direction, 50A a collimator control section for controlling the slit width $\omega$ of the collimator 150, 70 an X-ray detector (multi-row detector) in which a multiplicity (n~1,000) of X-ray detector elements are linearly arranged in the channel CH arrangement direction to form four rows L1–L4, for example, in the body axis direction, 80' a data collecting section (DAS) for generating projection data $g(X, \theta)$ of the subject based on channel detected signals of the X-ray detector 70 and collecting the data, and 30A a rotation control section for performing rotation control of the X-ray image capturing system (which will be sometimes referred to simply as a gantry hereinbelow). FIG. 1 additionally shows the x-, y- and z-coordinate axes fixed with respect to the scan gantry section 30, where the z-axis coincides with the body axis CLb direction.

In the operating console section 10, reference numeral 11 designates a central processing apparatus for performing main control and processing of the X-ray CT apparatus (such as scan planning, scan control, CT tomographic image reconstruction processing, etc.), 13 a display device (CRT) for displaying the scan plan, the scanned/reconstructed CT tomographic image and the like, 14 a control interface for exchanging several kinds of control signals C1, C2 and monitor signals between the central processing apparatus 11 and the scan gantry section 30 and imaging table 20, and 15 a data collection buffer for accumulating the projection data from the data collecting section 80'.

The operation will be now outlined. The X-ray fan beam XLFB from the X-ray tube 40 passes through the subject 100 and impinges upon all the detector rows L1–L4 of the X-ray detector 70. The data collecting section 80' generates corresponding projection data $g_1(X, \theta)$-$g_4(X, \theta)$ by integrating and A/D converting channel detected signal currents of the detector rows L1–L4, and stores the projection data in the data collection buffer 15. Next, similar projection is performed with the gantry slightly rotated to a view angle $\theta$, and so forth; thus collecting and accumulating the projection data for one rotation of the gantry.

Moreover, the imaging table 20 is intermittently/continuously moved in the body axis direction of the subject 100 according to an axial/helical scan scheme, and consequently, all the projection data of a required imaged region in the subject are collected and accumulated. The central processing apparatus 11 then reconstructs a CT tomographic image of the subject 100 based on the resulting projection data simultaneously with or after the scan operation, and displays the CT tomographic image on the display device 13.

Inset (a) shows a planar view of the conventional collimator 150. The collimator 150 has a structure such that two parallel slit plates 150a and 150b lying perpendicular to the z-axis are pivotally attached to two links 152a and 152b by pins 154 at the four corners to form a parallelogram, and the links 152a and 152b are pivotally supported by respective pivots 153a and 153b on a centerline CL of the links 152a and 152b. In this configuration, the slit width $\omega$ in the z-axis direction can be changed symmetrically with respect to the centerline CL by swiveling the pivot 153b of the link 152b right and left by a geared motor 155. The centerline CL of the slit width $\omega$ corresponds in position to a centerline CLd of the X-ray detector rows.

The conventional data collecting section 80' comprises a switch unit (SWU) 81' that can combine (add) the channel detected signal currents across the detector rows, and a data collecting unit (DAS1–DAS4) 82 that can generate four series of projection data $g_1(X, \theta)$-$g_4(X, \theta)$ by integrating and A/D converting channel combined currents output from the switch unit 81'. By combining the channel detected signal currents across the detector rows corresponding to a required slice width, the data collecting section 80' can reconstruct CT tomographic images symmetric with respect to the centerline CLd of the X-ray detector rows and having different slice widths, as will be described below. A conventional scan (projection) data collecting scheme for providing the different slice widths will be particularly described below.

FIG. 2 is a diagram for explaining a conventional data collecting scheme. Specifically, FIG. 2(A) shows a case in which channel detected signal currents i1–i4 of the detector rows L1–L4 are individually converted into projection data S1–S4 having a small slice width by DAS1–DAS4, without combining the channel detected signal currents i1–i4 across the detector rows. Thus, four CT tomographic images having a small slice width can be reconstructed in one scan. This data collecting scheme is suitable for imaging of minute tissues (in the head, lesion site, etc.) of the subject.

FIG. 2(B) shows a case in which channel detected signal currents i1 and i2 of the detector rows L1 and L2, and i3 and i4 of the detector rows L3 and L4 are added (combined) beforehand by the SWU 81', and then the combined signals are converted into projection data S1 and S2 having a relatively large slice width by, for example, DAS1 and DAS3. Thus, two CT tomographic images having a relatively large slice width can be reconstructed in one scan. This data collecting scheme is suitable for rather minutely checking for the presence of disorder in a relatively large imaged region (thorax, abdomen, etc.) of the subject.

FIG. 2(C) shows a case in which channel detected signal currents i1–i4 of all the detector rows L1–L4 are added (combined) beforehand by the SWU 81', and then the combined signal is converted into projection data S1 having a large slice width by, for example, DAS1. Thus, one CT tomographic image having a large slice width can be reconstructed in one scan. This data collecting scheme is suitable for broadly checking for the presence of disorder in a large imaging region (thorax—abdomen, etc.) of the subject. In any case, imaging by the four detector rows can be achieved during one scan, and the speed of the X-ray CT imaging can be increased.

However, since the conventional imaging pattern is symmetric and fixed as described above, it cannot be flexibly adapted to imaging for various medical purposes. Specifically, assume that there are requirements that the presence of disorder should be checked for broadly from the thorax to abdomen of the subject and that the main tissue should be minutely examined. To respond to such requirements in the conventional scheme, imaging with no gap must be performed first from the thorax to abdomen of the subject in the imaging pattern of FIG. 2(C), and then minute imaging of the main site of the subject must be performed in the imaging pattern of FIG. 2(A). Such two-time imaging is time-consuming and, in addition, the subject may be exposed to excessive radiation.

Moreover, since the conventional scheme combines (adds) the channel detected signals (currents) of the X-ray detector elements across the rows as they are, projection data of different slice widths cannot be simultaneously acquired from channel detected signals in a channel. Specifically, when the projection data S1 of FIG. 2(C) is acquired, for example, the projection data S1, S2 or S1–S4 of FIG. 2(B) or (A) cannot be simultaneously acquired. Similarly, when the projection data S1, S2 of FIG. 2(B) is acquired, the projection data S1–S4 of FIG. 2(A) cannot be simultaneously acquired.

SUMMARY OF THE INVENTION

The present invention was made considering the aforementioned problems in the prior art, and an object thereof is to provide an X-ray CT apparatus and method that can efficiently acquire projection data having a variety of slice widths (slice patterns) in one scan.

The object can be attained by a configuration shown in FIG. 3, for example. Specifically, in accordance with an aspect (1) of the present invention, there is provided an X-ray CT apparatus in which an X-ray tube 40 and an X-ray detector 70 are opposed to each other interposing a subject 100, in which detector a multiplicity of X-ray detector elements are linearly arranged in the channel arrangement direction to form a plurality of rows in the subject body axis direction, for reconstructing a CT tomographic image of the subject based on detected signals from the X-ray detector, comprising: signal duplicating means 81a for duplicating channel detected signals of the X-ray detector 70 and distributing the duplicated signals to a plurality of groups a, b, etc.; signal combining means 81b that can combine the distributed duplicated signals in each group in an arbitrary pattern across the detector rows for each channel; and data collecting means 82 for converting the channel combined signals for each group into projection data for each channel and collecting the projection data along the channel arrangement direction.

In the aspect (1) of the present invention, the configuration in which the channel detected signals of the X-ray detector 70 are duplicated and distributed to a plurality of groups enables projection data having different slice widths (slice patterns) to be simultaneously acquired for channel detected signals in a channel. Specifically, even when the projection data S1 of FIG. 2(C) is acquired, for example, the projection data S1, S2 or S1–S4 of FIG. 2(B) or (A) can be simultaneously acquired. Moreover, in the aspect (1) of the present invention, the configuration in which the duplicated signals in each of the groups a, b, etc. can be combined in an arbitrary pattern enables projection data having a variety of slice widths (slice patterns) to be simultaneously and efficiently acquired in one scan, and hence, the configuration can be adapted to imaging requirements according to various medical purposes.

The term "different slice widths" refers to a case in which the channel duplicated signals are combined across the detector rows in a continuous manner, and the term "slice pattern" refers to a case in which the channel duplicated signals are combined across the detector rows in a discontinuous manner (with gaps).

In accordance with another aspect (2) of the present invention, there is provided an X-ray CT apparatus having the same configuration as that set out in the preamble of the foregoing description of the aforementioned X-ray CT apparatus, comprising, as exemplarily shown in FIG. 17, signal duplicating means 81a for duplicating channel detected signals of the X-ray detector 70 and distributing the duplicated signals to a plurality of groups G1–G3, etc; signal combining means 81b that combines the distributed duplicated signals in each group in a predefined pattern across the detector rows for each channel; and data collecting means 82 for converting the channel combined signals for each group into projection data for each channel and collecting the projection data along the channel arrangement direction.

In the aspect (2) of the present invention, although the number of the slice widths (slice patterns) for the channel combined signals is limited, the signal duplicating means 81a and signal combining means 81b having a simple configuration enable projection data having a variety of slice widths (slice patterns) to be simultaneously and efficiently acquired in one scan.

In accordance with another aspect (3) of the present invention, there is provided an X-ray CT apparatus having the same configuration as that set out in the preamble of the foregoing description of the aforementioned X-ray CT apparatus, comprising, as exemplarily shown in FIG. 18, signal duplicating means 81a for duplicating channel detected signals of the X-ray detector 70 and distributing the duplicated signals to a plurality of groups G1–G6, etc; signal combining means 81b that combines the distributed duplicated signals in each group in a predefined pattern across the detector rows for each channel; signal selecting means 81c for further selecting from among the channel combined signals for the groups; and data collecting means 82 for converting the selected channel combined signals for each group into projection data for each channel and collecting the projection data along the channel arrangement direction.

In the aspect (3) of the present invention, the signal duplicating means 81a and signal combining means 81b having a relatively simple configuration enable the channel combined signals having various slice widths (slice patterns) to be generated beforehand, and by the configuration in which the channel combined signals are selected by the signal selecting means 81c, projection data having a variety of slice widths (slice patterns) can be simultaneously and efficiently acquired in one scan.

Preferably, in accordance with another aspect (4) of the present invention, the X-ray CT apparatus as described regarding the aspects (1)–(3) of the present invention further comprises data processing means (CPU) for combining the collected projection data for each group across the detector rows for each channel, as exemplarily shown in FIG. 12(B).

In the aspect (4) of the present invention, projection data having an additional different slice width (slice pattern) can be obtained by having the data processing means combine original projection data having a variety of slice widths (slice patterns) obtained in one scan. Therefore, projection data having a variety of slice widths (slice patterns) can be substantially simultaneously and efficiently acquired in one scan.

Preferably, in accordance with another aspect (5) of the present invention, the X-ray CT apparatus as described regarding the aspects (1)–(3) of the present invention comprises, as exemplarily shown in FIG. 5, image reconstructing means (represented by the CPU 11a) for performing image reconstruction of CT tomographic images based on the data from the data collecting means 82.

In the aspect (5) of the present invention, the data collecting means 82 enables the projection data having a variety of slice widths (slice patterns) to be quickly collected by hardware, and the image reconstructing means (CPU 11a) can exclusively concentrate on its fundamental task of image reconstruction processing. Therefore, the processing load on the CPU can be significantly reduced.

Preferably, in accordance with another aspect (6) of the present invention, in the X-ray CT apparatus as described regarding the aspects (1)–(3) of the present invention, the X-ray detector 70 comprises a multiplicity of X-ray detector elements linearly arranged in the channel arrangement direction to form a plurality of rows of equal detection width in the subject body axis direction, as exemplarily shown in FIG. 14.

Preferably, in accordance with another aspect (7) of the present invention, in the X-ray CT apparatus as described regarding the aspects (1)–(3) of the present invention, the X-ray detector 70 comprises a multiplicity of X-ray detector elements linearly arranged in the channel arrangement direction to form a plurality of rows having different detection widths in the subject body axis direction, as exemplarily shown in FIG. 15.

Preferably, in accordance with another aspect (8) of the present invention, in the X-ray CT apparatus as described regarding the aspects (1)–(3) of the present invention, the signal duplicating means 81a comprises current mirror circuits for duplicating the channel detected signal currents of the X-ray detector elements identically or in a constant ratio, as exemplarily shown in FIG. 6. Thus, one or more duplicated signal currents that are the same as or proportional to a reference current based on a channel detected signal current can be efficiently produced.

Preferably, in accordance with another aspect (9) of the present invention, in the X-ray CT apparatus as described regarding the aspect (1) of the present invention, the signal combining means 81b comprises a plurality of switching means for individually ON/OFF controlling the duplicated signals for each group by an external control signal; and a signal combining circuit for combining output signals from the switching means for each group, as exemplarily shown in FIG. 6. Thus, combined signals can be easily generated in arbitrary combination patterns.

Preferably, in accordance with another aspect (10) of the present invention, in the X-ray CT apparatus as described regarding the aspect (3) of the present invention, the signal selecting means 81c comprises a plurality of switching means for individually ON/OFF controlling the channel combined signals for each group by an external control signal; and a signal combining circuit for combining output signals from the switching means for each group, as exemplarily shown in FIG. 18. Thus, combined signals can be easily selected and further combined in arbitrary combination patterns.

Preferably, in accordance with another aspect (11) of the present invention, the X-ray CT apparatus as described regarding the aspect (1) of the present invention comprises an X-ray detector 70 having k detector rows; and m ($\geq 2$) signal duplicating/combining units 81a, 81b, etc. including a set of signal duplicating means and signal combining means that can perform signal processing for the k/m detector rows, as exemplarily shown in FIG. 16, so that the signal processing for the k detector rows of the X-ray detector are processed in parallel by the m signal duplicating/combining unit.

In the aspect (11) of the present invention, since a plurality of basic signal duplicating/combining units 81a, 81b, etc. are provided in parallel, the present invention can be easily applied to an X-ray detector 70 having many detector rows.

Preferably, in accordance with another aspect (12) of the present invention, the X-ray CT apparatus as described regarding the aspects (1)–(3) of the present invention comprises collimator means 50 interposed between the X-ray tube 40 and X-ray detector 70 that can change the X-ray beam width in the subject body axis direction asymmetrically on both the sides of a center (CLd) of the X-ray detector in the body axis CLb direction, as exemplarily shown in FIG. 3.

Preferably, in accordance with another aspect (13) of the present invention, in the X-ray CT apparatus as described regarding the aspect (12) of the present invention, the collimator means 50 comprises two parallel slit plates 50a and 50b for limiting the X-ray beam width in the subject body axis direction so that slit widths $\omega a$ and $\omega b$ formed between respective slit plates and a line assumed to lie on the center CLd of the X-ray detector in the body axis direction can be individually changed, as exemplarily shown in FIG. 4.

Preferably, in accordance with another aspect (14) of the present invention, the X-ray CT apparatus as described regarding the aspects (1)–(3) of the present invention further comprises display means 13A for displaying information about a scan plan, and displays marker information S1, S2, etc. of the subject slice positions and/or slice widths on the display means corresponding to combination patterns across the detector rows specified by previously performed scan planning, as exemplarily shown in FIG. 8. Thus, the radiologist, for example, can easily specify and confirm complex scan plans (parameters) taking different slice widths (slice patterns) into account.

In accordance with another aspect (15) of the present invention, there is provided a projection data collecting method for use with an X-ray CT apparatus having the configuration such as that set out in the preamble of the foregoing description of the aforementioned X-ray CT apparatus, comprising duplicating channel detected signals of the X-ray detector and distributing the duplicated signals to a plurality of groups; combining the duplicated signals in each group in an arbitrary pattern across the detector rows for each channel to generate a series of projection data; and simultaneously collecting the projection data having different slice widths based on the channel detected signals in a channel.

In accordance with another aspect (16) of the present invention, there is provided an X-ray CT imaging method employing the X-ray CT apparatus as described regarding the aspects (1)–(3) of the present invention, comprising the steps of: previously specifying combination patterns of channel detected signals across the detector rows during scan planning; and generating/collecting projection data of corresponding slice patterns by performing combination of the channel detected signals across the detector rows according to the specified combination patterns during a subsequent scan.

As described above, according to the present invention, since projection data having a variety of slice widths (slice patterns) can be efficiently acquired in one scan, the present invention can be flexibly adapted to imaging requirements of various medical purposes, and can greatly contribute to improvement of the speed and convenience in X-ray CT medical services.

Further objects and advantages of the present invention will be apparent from the following description of the preferred embodiments of the invention as illustrated in the accompanying drawings.

BRIEF DESCRIPTION OF THE DRAWINGS

FIG. 18 is a diagram for explaining data collecting patterns in a sixth embodiment.

DETAILED DESCRIPTION OF THE INVENTION

Several preferred embodiments of the present invention will now be described in detail with reference to the accompanying drawings, throughout which identical reference symbols designate identical or corresponding portions.

Figure 1:
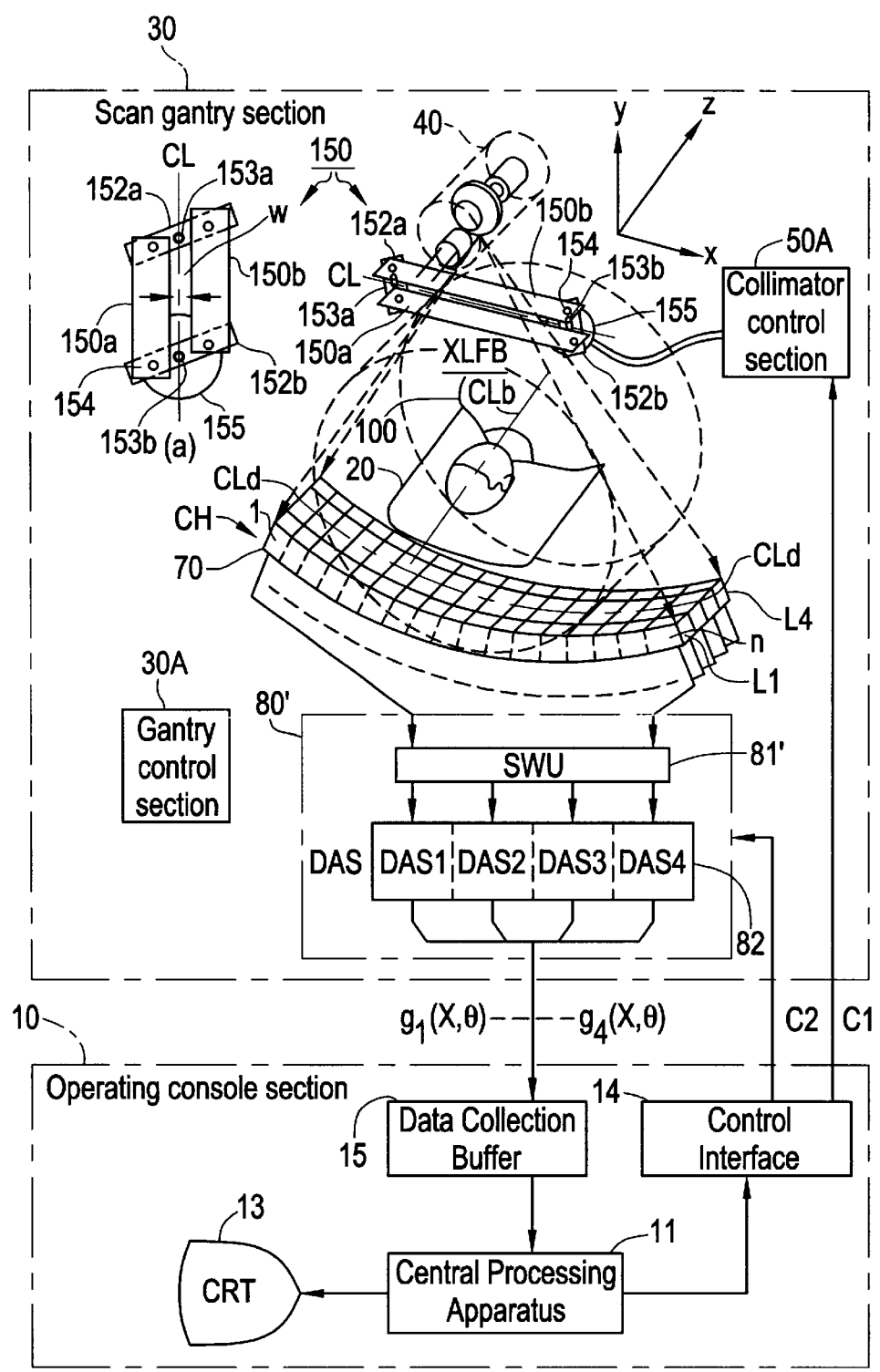
FIG. 1 is a configuration diagram of the main portion of a conventional X-ray CT apparatus.
Figure 2A:
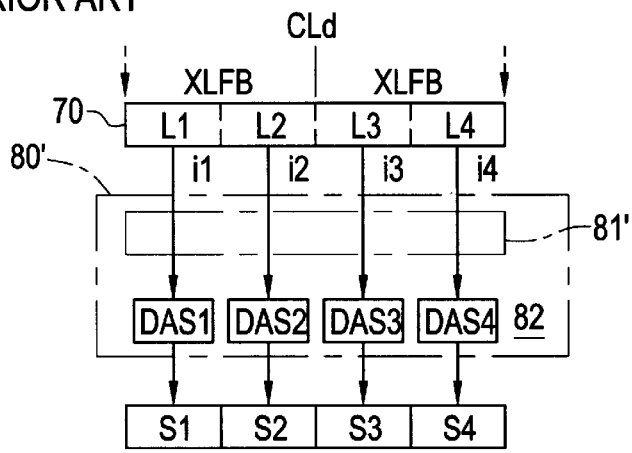
FIG. 2 is a diagram for explaining a conventional data collecting scheme.
Figure 2B:
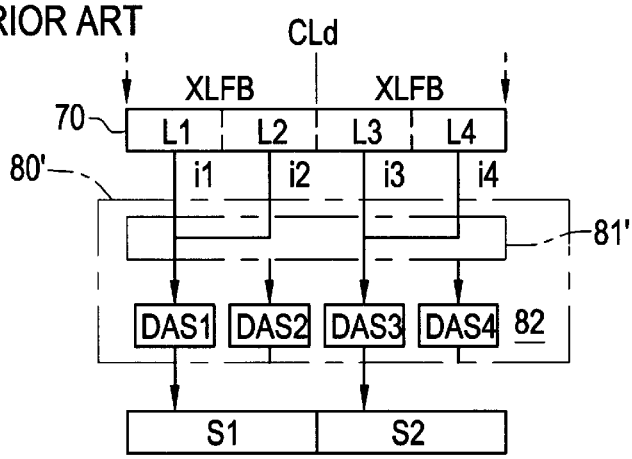
Figure 2C:
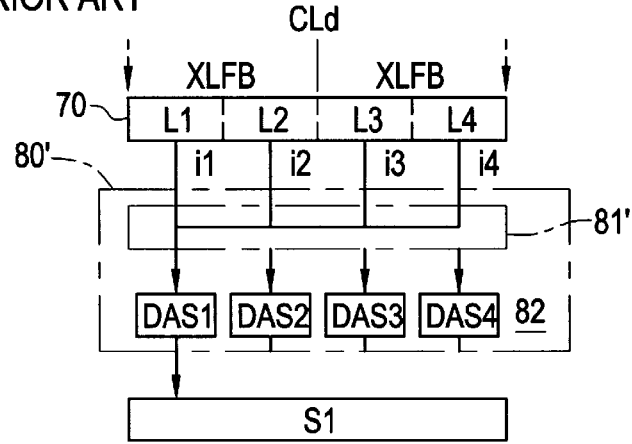
Figure 3:
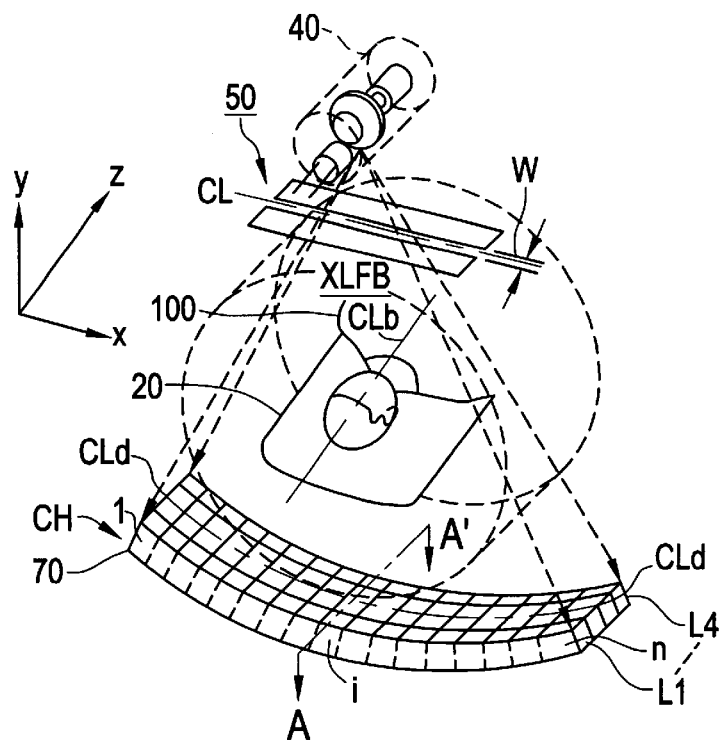
FIG. 3 is a diagram for explaining the principle of the present invention.
Figure 3:
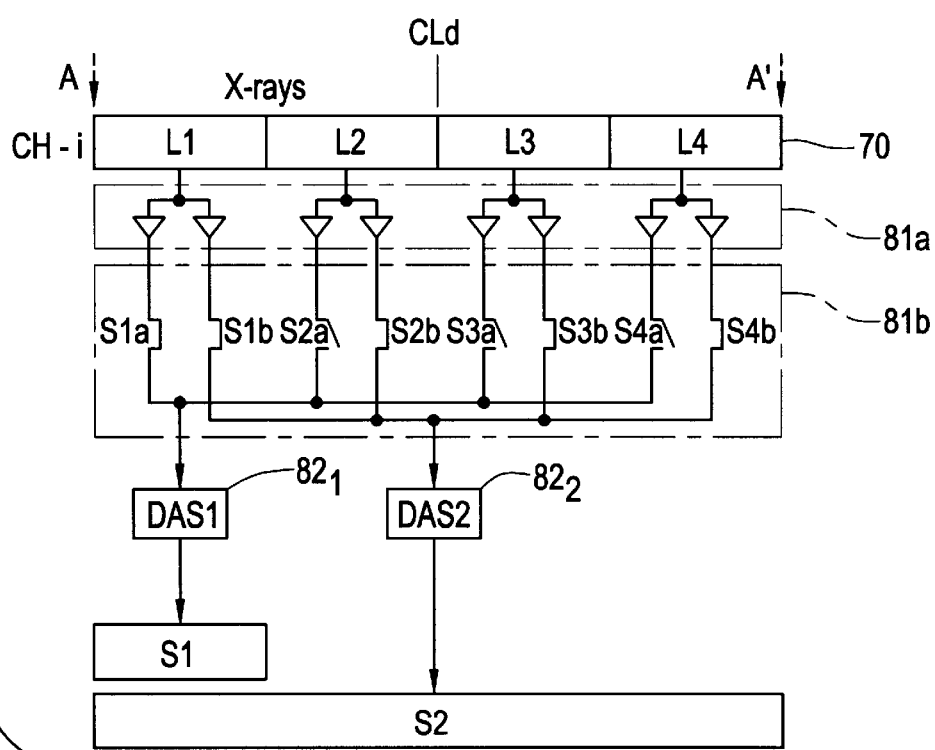
Figure 4:
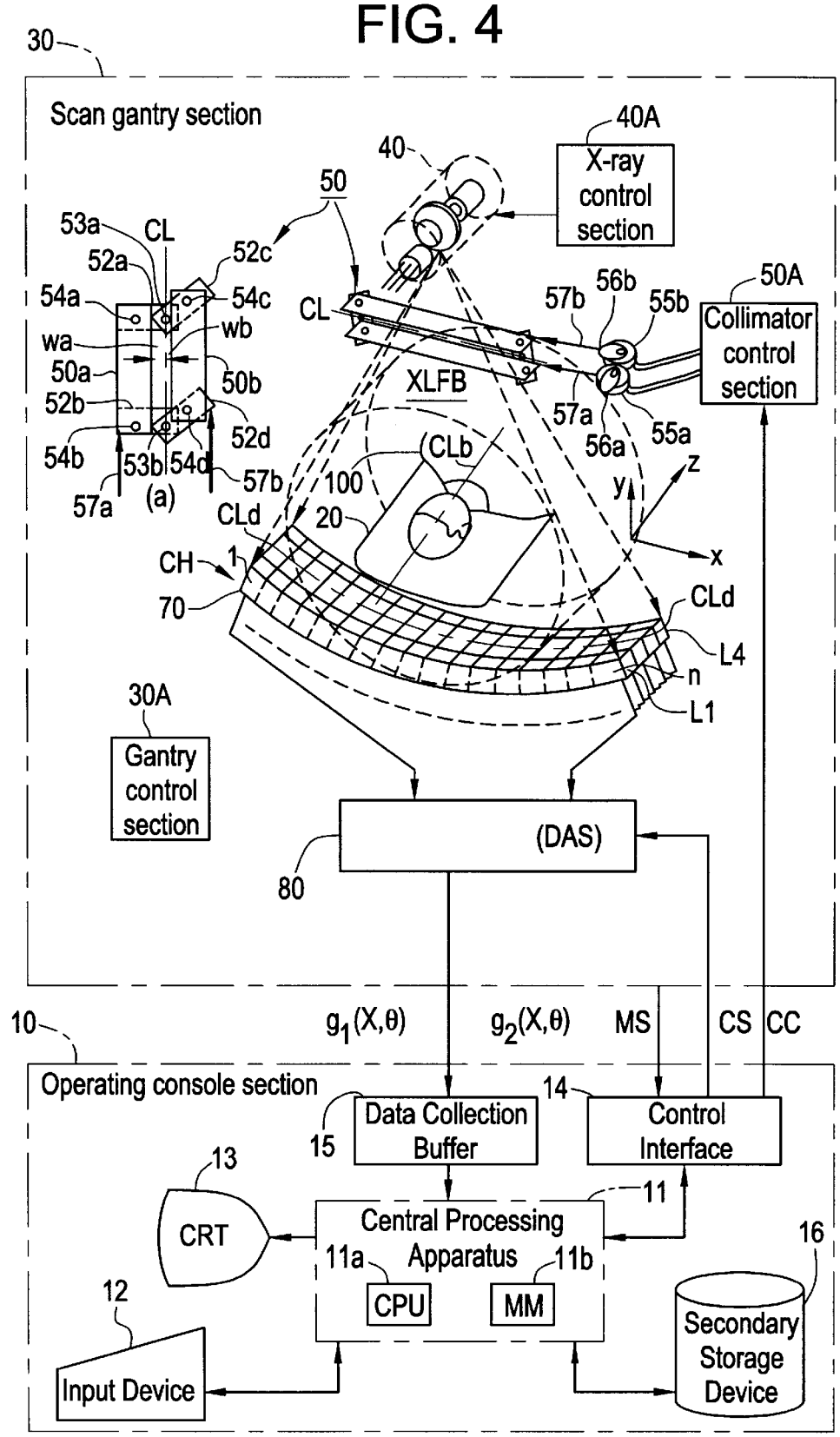
FIG. 4 is a configuration diagram of the main portion of an X-ray CT apparatus in one embodiment.

FIG. 4 is a configuration diagram of the main portion of an X-ray CT apparatus in one embodiment, in which reference numeral 30 designates a scan gantry section, 50 a collimator that can asymmetrically limit the irradiation width of X-rays in the body axis direction, 50A a collimator control section, 70 an X-ray detector (multi-row detector), 80 a data collecting section (DAS) for generating projection data $g_1(X, \theta)$, $g_2(X, \theta)$ of the subject based on the detected signals from the X-ray detector 70 and collecting the projection data, 11 a central processing apparatus for performing main control and processing of the X-ray CT apparatus, 11a a CPU of the central processing apparatus 11, 11b a main memory (MM) comprising a RAM, ROM, etc. employed by the CPU 11a, and 16 a secondary storage device (hard disk device or the like) for accumulating and storing the projection data from a data collection buffer 15, and storing several application programs needed for controlling/operating the X-ray CT apparatus and data files for several calculations and corrections and the like. Parts of the configuration other than those described above may be the same as described regarding FIG. 1.

The inset (a) shows a planar view of an exemplary collimator 50. The collimator 50 comprises, on the one hand, a slit plate 50a disposed in parallel with a centerline CL assumed to lie normal to the z-axis. The slit plate 50a is pivotally attached to two links 52a and 52b by two pins 54a and 54b and two common pivots 53a and 53b so that the centerline CL, the slit plate 50a and the links 52a and 52b form a parallelogram. Moreover, the end of the link 52b is reciprocated by an eccentric cam 56a fixed to the rotation axis of a geared motor 55a and a link mechanical portion 57a cooperating with the cam 56a, thus enabling a slit width ωa formed by the slit plate 50a and the centerline CL in the z-axis direction to be independently changed.

On the other hand, the collimator 50 comprises a slit plate 50b disposed in parallel with the centerline CL. The slit plate 50b is pivotally attached to two links 52c and 52d by two pins 54c and 54d and the two common pivots 53a and 53b so that the centerline CL, the slit plate 50b and the links 52c and 52d form a parallelogram. Moreover, the end of the link 52d is reciprocated by an eccentric cam 56b fixed to the rotation axis of a geared motor 55b and a link mechanical portion 57b cooperating with the cam 56b, thus enabling a slit width ωb formed by the slit plate 50b and the centerline CL in the z-axis direction to be independently changed.

The centerline CL assumed in the collimator 50 corresponds in position to the centerline CLd of the X-ray detector rows. Therefore, by individually controlling the slit plates 50a and 50b, the X-ray beam widths (corresponding to ωa and ωb) in the body axis direction impinging upon the X-ray detector 70 can be changed asymmetrically with respect to the centerline CLd. Thus, the subject 100 never needs to be exposed to more than the minimum required amount of X-rays, and excessive exposure to the subject 100 can be effectively avoided.

Figure 5:
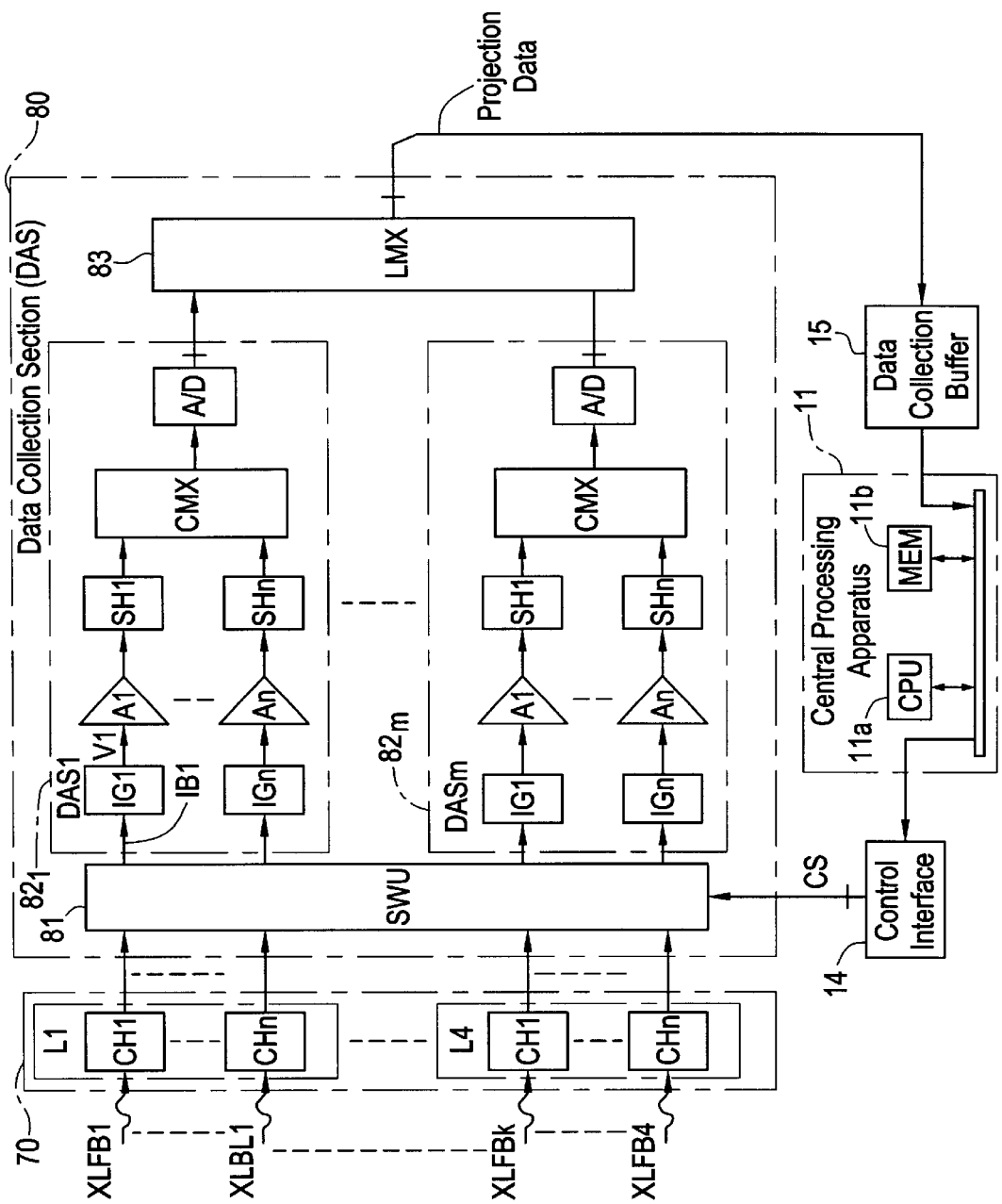
FIG. 5 is a diagram showing the configuration of a data collecting/calculating system in one embodiment.

FIG. 5 is a diagram showing the configuration of a data collecting/calculating system in one embodiment, illustrating a general configuration in which in series of projection data of arbitrary slice widths (slice patterns) can be simultaneously collected based on the channel detected signals for k rows of the X-ray detector 70. In the data collecting section 80, reference numeral 81 designates a switch unit (SWU) that duplicates the channel detected signals from the X-ray detector 70 and can combine the duplicate signals in arbitrary patterns across the detector rows, which will be described later in detail with reference to FIG. 6. Reference numerals $82_1$–$82_m$ designate data collecting units DAS1-DASm for generating and collecting respective projection data based on the combined signals output from the SWU 81.

Now consider the signal processing by the DAS1. An input channel detected (combined) signal current IB1 is integrated by a mirror integrator IG1 and converted into a signal voltage V1 proportional to a transmitted radiation quantity. The voltage is amplified by an amplifier A1 if necessary, and sample-held by a sample holding circuit SH1 at predetermined timing. Such a process applies to the signal processing for the channels CH2-CHn. Moreover, output signals from the sample holding circuits SH1-SHn are multiplexed by a channel signal multiplexer CMX, and A/D converted by an A/D converter A/D. Such a process applies to signal processing by the data collecting units DAS2-DASm. Furthermore, output data from the data collecting units DAS1-DASm are multiplexed by a row multiplexer LMx, and the resulting series of projection data (scan data) is temporarily accumulated in the data collection buffer 15.

By such a configuration, the CPU 11a establishes and controls combination patterns of duplicated signals for the switch unit 81 according to scan parameter information (slice widths, slice patterns) specified by a scan plan in advance. Thereafter, a scan is performed to obtain projection data having desired slice widths (slice patterns). Some exemplary scan (projection) data collecting schemes in accordance with the present invention will concretely described hereinbelow.

Figure 6:
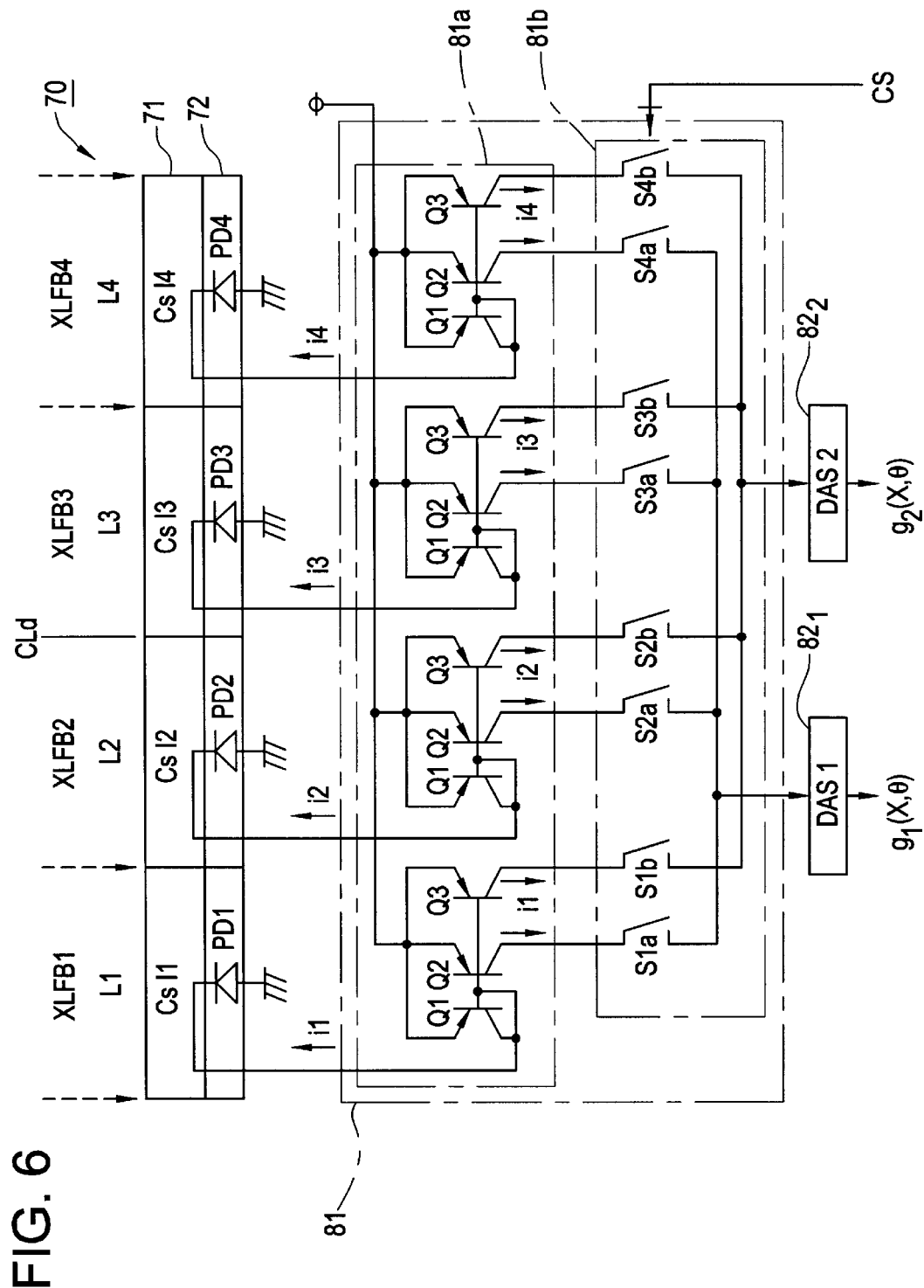
FIG. 6 is a diagram for explaining a data collecting scheme in accordance with a first embodiment.

FIG. 6 is a diagram for explaining a data collecting scheme in accordance with a first embodiment, showing a case in which two series of projection data of arbitrary slice widths (slice patterns) can be simultaneously collected based on the channel detected signals for four rows. FIG. 6 shows a cross-sectional view of detector elements in a channel in the X-ray detector 70 across rows. Reference symbols L1–L4 designate detector rows, and X-ray fan beams XLFB1–XLFB4 are projected together expanding symmetrically of the body axis direction with respect to the centerline CLd of the detector rows L1–L4.

The X-ray detector 70 comprises a scintillator layer 71 on the front side and a photodiode layer 72 on the back side, and these layers are divided into picture elements (i.e., into rows and channels). The scintillator 71 contains, for example, cesium iodide CsI as a fluorescent material with low light scattering, and converts the X-rays passing through the subject into light (X-ray photons). The photodiode (PD) 72 converts the converted light into a charge (current).

The switch unit 81 comprises a signal duplicating section 81a for duplicating and distributing the channel detected signals of the X-ray detector 70 and a signal combining section 81b that can combine (add) the duplicated channel detected signals in arbitrary patterns across the detector rows.

An exemplary signal duplicating circuit includes a current mirror circuit comprised of transistors Q1–Q3 having uniform characteristics. When a channel detected signal current (reference current) i1 is applied to Q1, the identical (or proportional) duplicated currents i1, i1 are applied to Q2 and Q3, respectively. In this case, since both the transistors Q2 and Q3 act as constant current sources, the original reference current i1 and the duplicated currents i1, i1 are not affected by the way their load has been connected (combined). That is, the duplicated currents i1, i1 can be separately distributed.

On the other hand, the signal combining section 81b is provided with m (in this example, m is 2) basic combining circuits, each including switches S1–S4 in series with the input lines and a conductor pattern circuit that can combine (add) the duplicated signals i1–i4 selected in respective lines.

By such a configuration, when a light impinges upon an inversely biased p-n junction of the photodiode PD1, a light current i1 proportional to a transmitted radiation quantity is generated, which current i1 is duplicated in the transistors Q2 and Q3, and the duplicated currents are separately distributed. The same process applies to PD2–PD4. Moreover, by selecting/combining as desired one of groups of the duplicated currents i1–i4 by the switches S1a–S4a, a combined current IB1a corresponding to an arbitrary slice width (slice pattern) is generated, and the current IB1a is converted into the projection data $g_1(X, \theta)$ in the data collecting unit DAS1. Similarly, by selecting/combining as desired the other of groups of the duplicated signals i1–i4 by the switches S1b–S4b, a combined current IB1b corresponding to another arbitrary slice width (slice pattern) is generated, and the current IB1b is converted into the projection data $g_2(X, \theta)$ in the data collecting unit DAS2. Thus, the two series of projection data $g_1(X, \theta)$ and $g_2(X, \theta)$ having arbitrary slice widths (slice patterns) can be simultaneously obtained by the simple configuration, and these projection data can be simultaneously CT-reconstructed.

While the current mirror circuit is described in the foregoing as being comprised of the transistors Q1–Q3, it is not limited thereto. Instead, the current mirror circuit may be made from field effect transistors (FETs). Moreover, the number of currents to be duplicated/distributed can be arbitrarily increased by increasing the number of transistors (or FETs). At the same time, the number of arbitrary slice widths (slice patterns) to be simultaneously obtained can be increased by increasing the number of the signal combining circuits 81b and DAS's.

Furthermore, although the preceding description is made on a case in which channel detected signal currents are duplicated and distributed, the present invention is not limited thereto. Instead, channel detected signal voltages may be duplicated and distributed.

Figure 7:
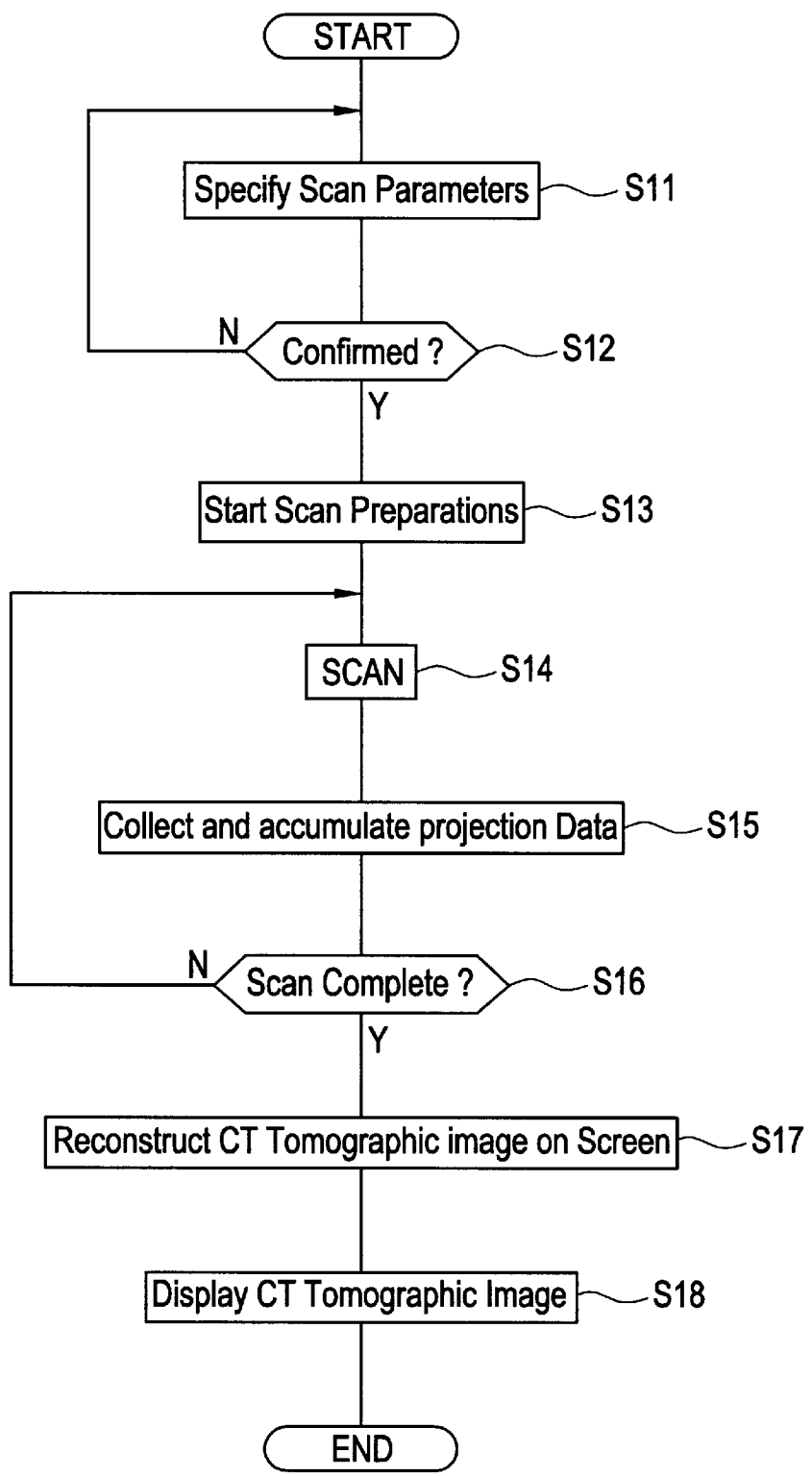
FIG. 7 is a flow chart of X-ray CT imaging processing in one embodiment.

Now the operation of X-ray CT imaging by such a configuration will be described. FIG. 7 is a flow chart of X-ray CT imaging processing in one embodiment, which is executed by the CPU 11a. Preferably, a scout scan (which is the same as traditional X-ray imaging) is preparatorily performed on the subject 100, and then the present processing is entered. In Step S11, a radiologist specifies scan parameters for a subsequent axial/helical scan on the subject 100.

Figure 8:
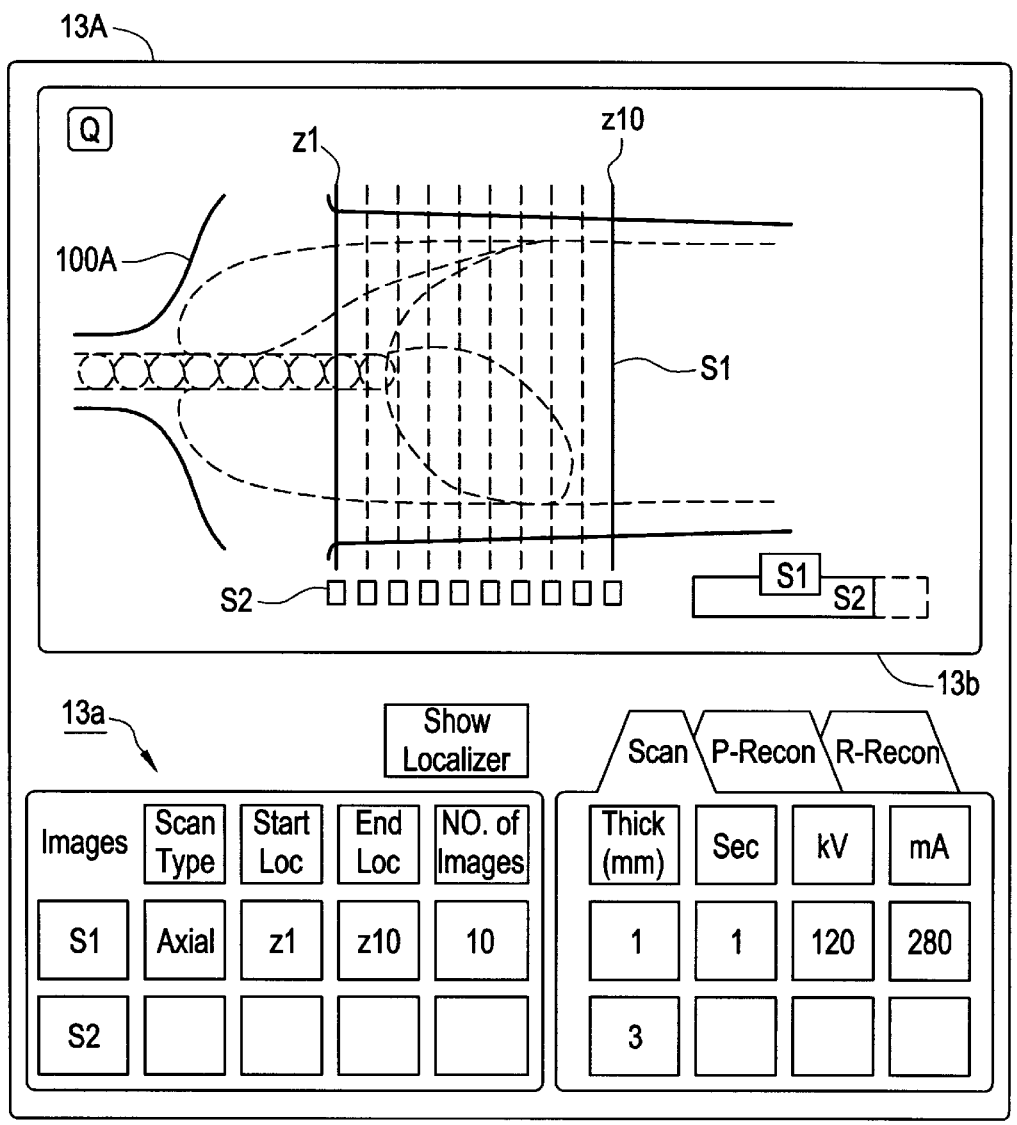
FIG. 8 is a pictorial diagram of scan parameter specifying processing in one embodiment.

FIG. 8 shows a pictorial diagram of the scan parameter specifying processing in one embodiment. After the preparatory scout scan is finished, a scan parameter specifying sheet 13a for the subsequent axial/helical scan is displayed on a display screen 13A, and the radiologist inputs the required scan parameters such as by clicking a mouse or by using keys. An exemplary scan plan for acquiring a CT tomographic image Q of the subject can be specified by identifying two types of scan schemes (slice widths, slice patterns) S1 and S2, as follows:

"Scan Plan S1":
    Scan Type    [Scan Type]    = Axial Scan,
    Scan start position on the body axis    [Start Loc]  = z1,
    Scan end position on the body axis    [End Loc]  = z10,
    Number of scans  [No. of Images]  = 10,
    Slice width for the subject   [Thick]  = 1 mm,
    Scan Time  [Sec]  = 1 sec/gantry rotation,
    Tube voltage of the X-ray tube  [kV]  = 120 kV,
    Tube current of the X-ray tube  [mA]  = 280 mA; and
"Scan Plan S2":
    Slice width for the subject   [Thick]  = 3 mm.

Moreover, when the radiologist clicks on a [Show Localizer] icon on the scan specifying sheet, a scout image 100A of the subject 100 as shown is displayed in an image display area 13b of the display screen 13A, and lines (cut lines) indicating the slice positions are superimposed. The bold lines in the drawing indicate the start and end positions in the scan plan S1, and dotted lines indicate the in-between slice positions. The slice width=1 mm is indicated by the corresponding line width. Marks "□" displayed in the lower portion of the scan plan S1 indicate the start slice position through end slice position of the scan plan S2. The slice width=3 mm (1 mm of S1 plus 1 mm each on the front and rear) is indicated by the display positions and widths of the corresponding mark "□".

Preferably, as shown, for example, the positional correspondence between the slice width S1 and slice width S2 is precisely displayed after magnification in part of the image display area 13b, along with the width that can be detected by all the detector rows of the X-ray detector 70 (indicated by a dotted line). Thus, the radiologist can clearly recognize the two scan plans that are to be simultaneously executed. Moreover, in this case, the radiologist can change the scan plans S1 and S2 as desired by viewing the scout image 100A on the image display area 13b to confirm the cut lines and the like, and if necessary, using the mouse or keyboard.

Returning to FIG. 7, at Step S12, the process waits for an operation of a confirmation "CONFIRM" button by the radiologist, and upon the operation of the "CONFIRM" button, imaging preparation is started according to the specified scan parameters at Step S13. Specifically, the collimator 50 is set at a specified slit width ω (symmetric/asymmetric). Moreover, the switch connections in the signal combining section 81b are set to establish slice widths (slice patterns) corresponding to the scan plans S1 and S2. Besides, the X-ray tube 40 is turned on, rotation of the gantry is started, and the subject is carried to a specified scanning position.

After the scan preparation is finished, a scan and reading is performed on the subject 100 at Step S14. At Step S15, projection data for the subject 100 is collected and accumulated. At Step S16, a decision is made as to whether the scan has been completed over the required imaging region, and if it has not, the process goes back to Step S14. When the scan is completed, an X-ray CT tomographic image of the subject 100 is reconstructed according to prespecified reconstruction parameters (P-Recon) at Step S17. At Step S18, the resulting X-ray CT tomographic image is displayed on the display section 13.

Figure 9A:
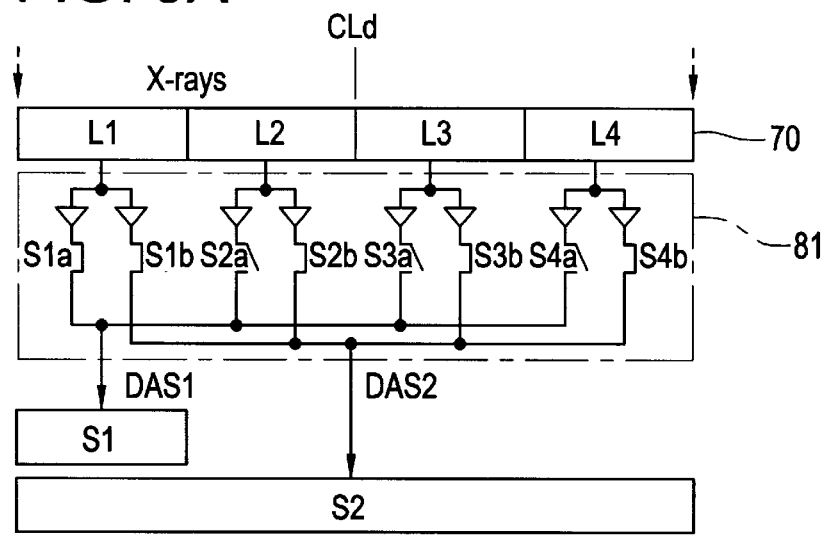
FIG. 9 is a diagram (1) for explaining data collecting patterns in the first embodiment.

Next, several typical collecting patterns of projection data will be concretely described. FIGS. 9–13 are diagrams (1)–(5) for explaining data collecting patterns in a first embodiment. FIG. 9 shows a case in which projection data S1 having a small slice width corresponding to one detector row and projection data S2 having a large slice width corresponding to four detector rows are simultaneously collected. In FIG. 9(A), by turning ON only a switch S1a of a group a, the projection data S1 having the small slice width corresponding in position to the detector row L1 is obtained. Moreover, by turning ON switches S1b–S4b of a group b together, the projection data S2 having the large slice width in which the channel detected signals of the detector rows L1–L4 are combined (added) is obtained. In such a case, since the channel detected signal current of the detector row L1 is duplicated and distributed at the signal duplicating section 81a, a process of employing one of the duplicated signals solely for S1 and employing the other for S2 after combination can be easily achieved. Moreover, in this case, it is known by the CPU 11a that the channel combined signal of the group b is enhanced (for example, four times the single signal), the CPU 11a can easily perform appropriate adjustment (averaging, etc.) of the detection sensitivity later.

Figure 9B:
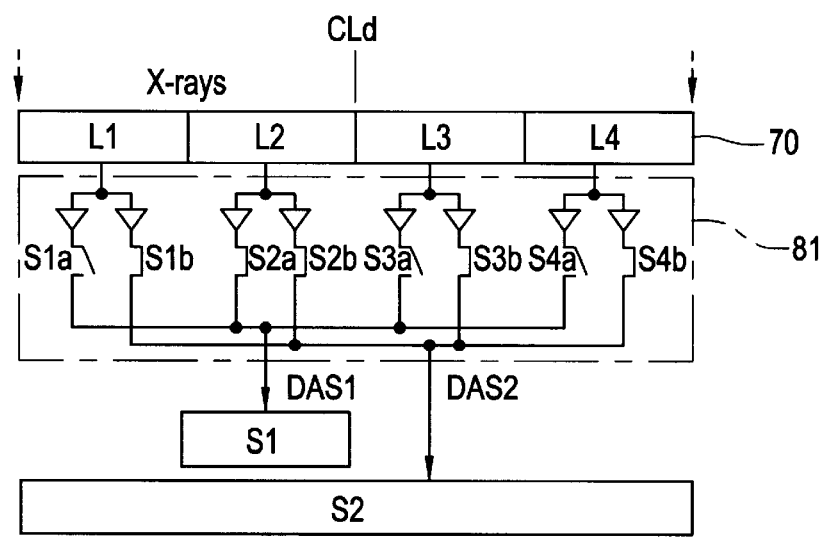

In FIG. 9(B), by turning ON only the switch S2a, instead of turning ON only the switch S1a, of the group a, projection data S1 having the small slice width is simultaneously obtained generally in the center of the projection data S2 having the large slice width.

Figure 9C:
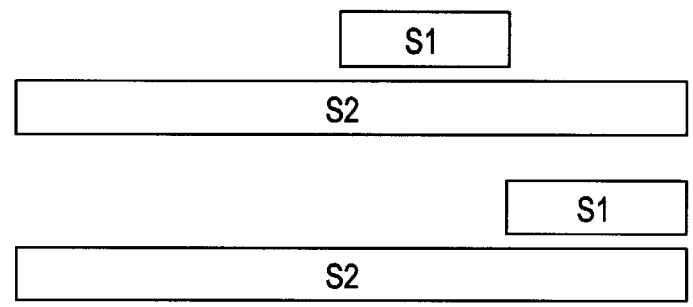

In FIG. 9(C), by turning ON only the switch S3a or S4a of the group a similarly to above, a corresponding data collecting pattern can be obtained.

Figure 10A:
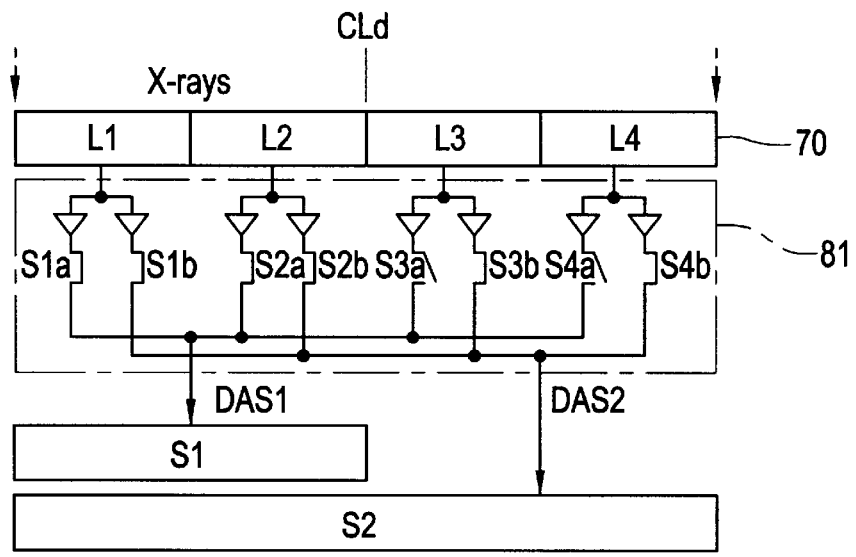
FIG. 10 is a diagram (2) for explaining data collecting patterns in the first embodiment.

FIG. 10 shows a case in which projection data S1 having a relatively small slice width corresponding to two detector rows and projection data S2 having a large slice width corresponding to four detector rows are simultaneously collected. In FIG. 10(A), by turning ON only the switches S1a and S2a of the group a, the projection data S1 having the relatively small slice width in which the channel detected signals of the detector rows L1 and L2 are combined (added) is obtained. The projection data S2 of the group b is the same as above.

Figure 10B:
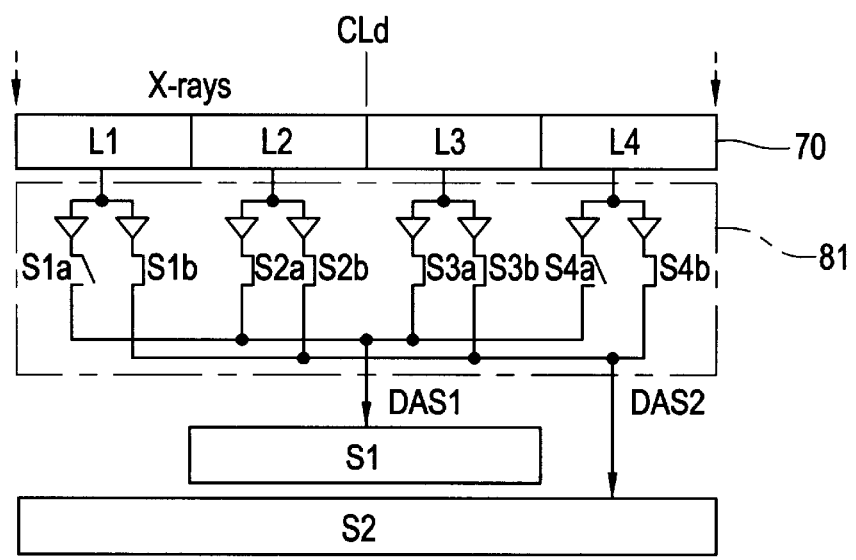

In FIG. 10(B), by turning ON only the switches S2a and S3a, instead of turning ON only the switches S1a and S2a, of the group a, projection data S1 having the relatively small slice width is simultaneously obtained just in the center of the projection data S2 having the large slice width.

Figure 10C:
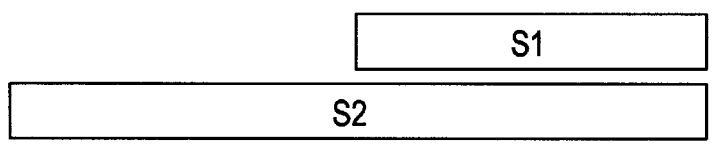

In FIG. 10(C), by turning ON only the switches S3a and S4a of the group a similarly to above, a corresponding data collecting pattern can be obtained.

Figure 11A:
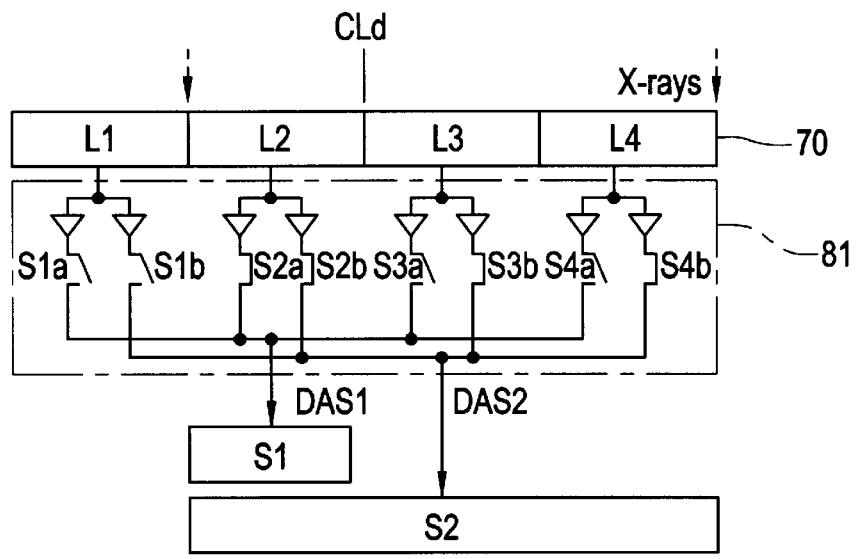
FIG. 11 is a diagram (3) for explaining data collecting patterns in the first embodiment.

FIG. 11 shows a case in which projection data S1 having a small slice width corresponding to one detector row and projection data S2 having a relatively large slice width corresponding to three detector rows are simultaneously collected. In FIG. 11(A), by turning ON only the switch S2a of the group a, the projection data S1 having the small slice width corresponding in position to the detector row L2 is obtained. Moreover, by turning ON the switches S2b–S4b of the group b together, the projection data S2 having the relatively large slice width in which the channel detected signals of the detector rows L2–L4 are combined (added) is obtained. At the same time, the slit width ω of the collimator 50 (the X-ray fan beam width) is limited within the range of the detector rows L2–L4, as shown, to effectively restrain excessive radiation exposure to the subject 100.

Figure 11B:
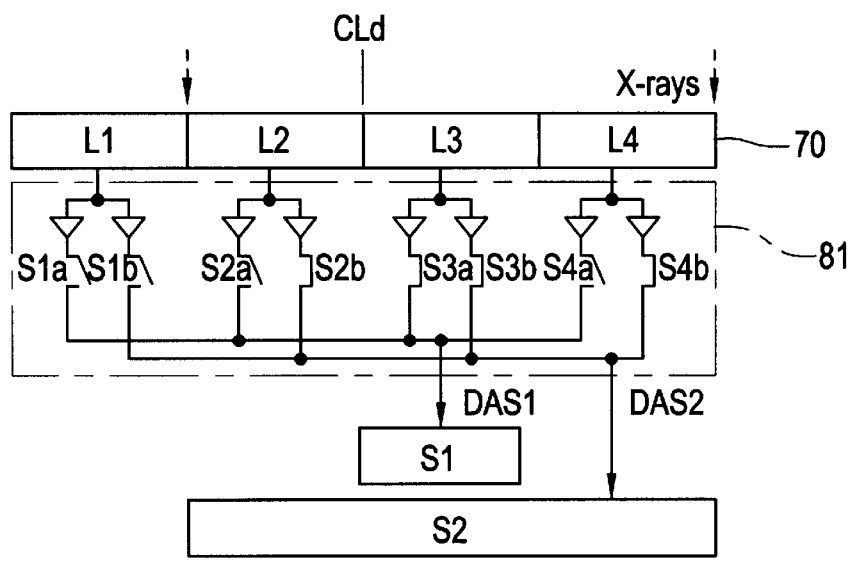

In FIG. 11(B), by turning ON only the switch S3a, instead of turning ON only the switch S2a, of the group a, projection data S1 having the small slice width is simultaneously obtained just in the center of the projection data S2 having the relatively large slice width.

Figure 11C:
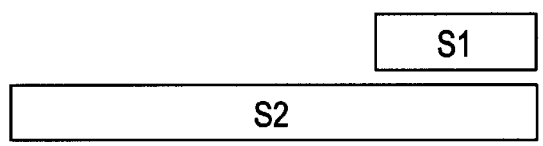

In FIG. 11(C), by turning ON only the switch S4a of the group a similarly to above, a corresponding data collecting pattern can be obtained.

Figure 12A:
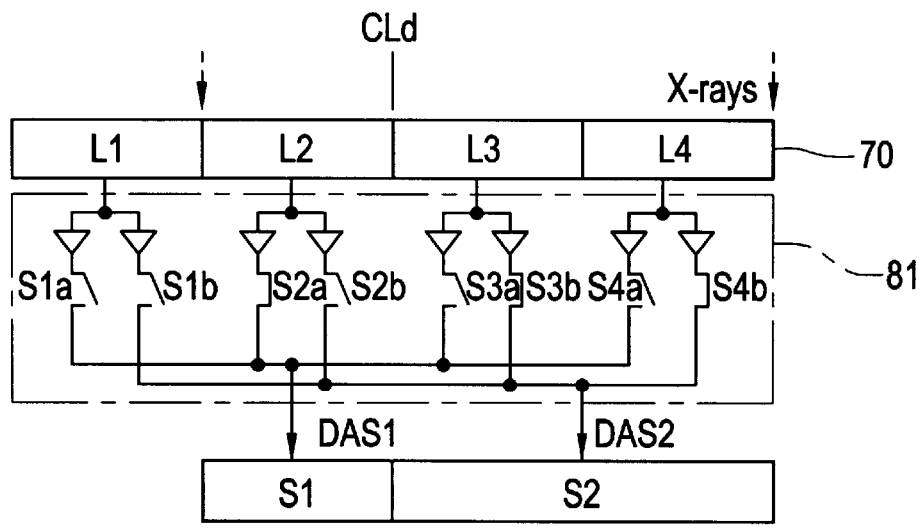
FIG. 12 is a diagram (4) for explaining data collecting patterns in the first embodiment.

FIG. 12 shows a case in which projection data S1 having a small slice width corresponding to one detector row and projection data S2 having a relatively small slice width corresponding to two detector rows are simultaneously collected so that the projection data S1 and S2 do not overlap each other. In FIG. 12(A), by turning ON only the switch S2a of the group a, the projection data S1 having the small slice width corresponding in position to the detector row L2 is obtained. Moreover, by turning ON the switches S3b and S4b of the group b, the projection data S2 having the relatively small slice width in which the channel detected signals of the detector rows L3 and L4 are combined (added) is obtained.

Figure 12B:
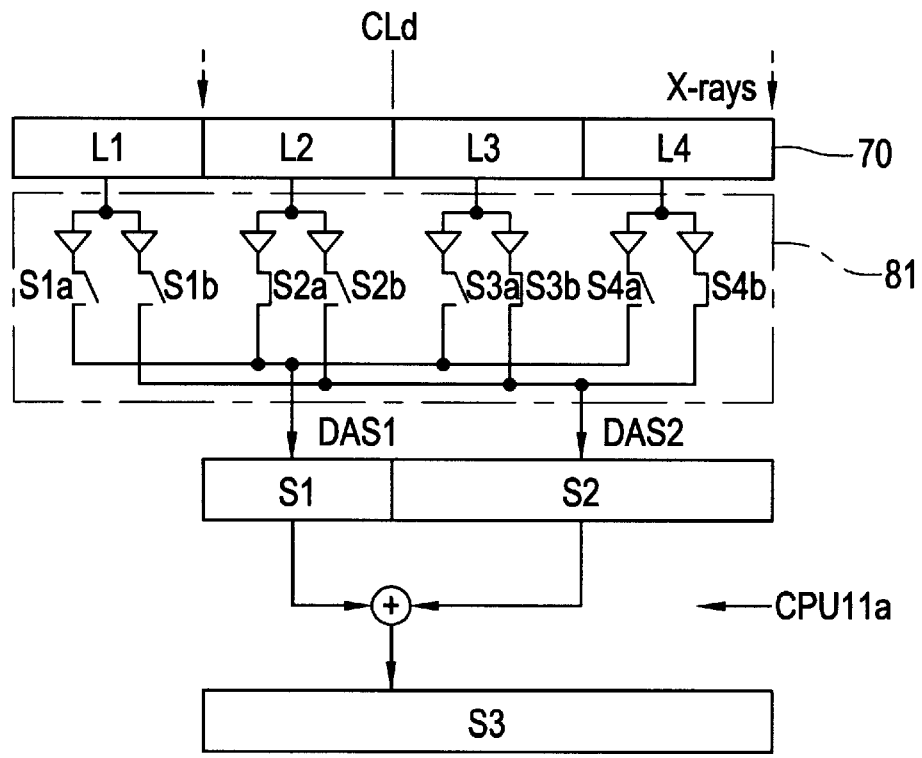

In FIG. 12(B), first, the CPU 11a can reconstruct respective CT tomographic images having the small slice width and relatively small slice width based on the resulting projection data S1 and S2. The CPU 11a can further reconstruct a CT tomographic image having the relatively large slice width corresponding to the three detector rows by combining (adding and averaging) the projection data S1 and S2 by data processing. Even in this case, since the original projection data S1 and S2 have been obtained by hardware, the processing load on the CPU 11a is significantly reduced.

Figure 13:
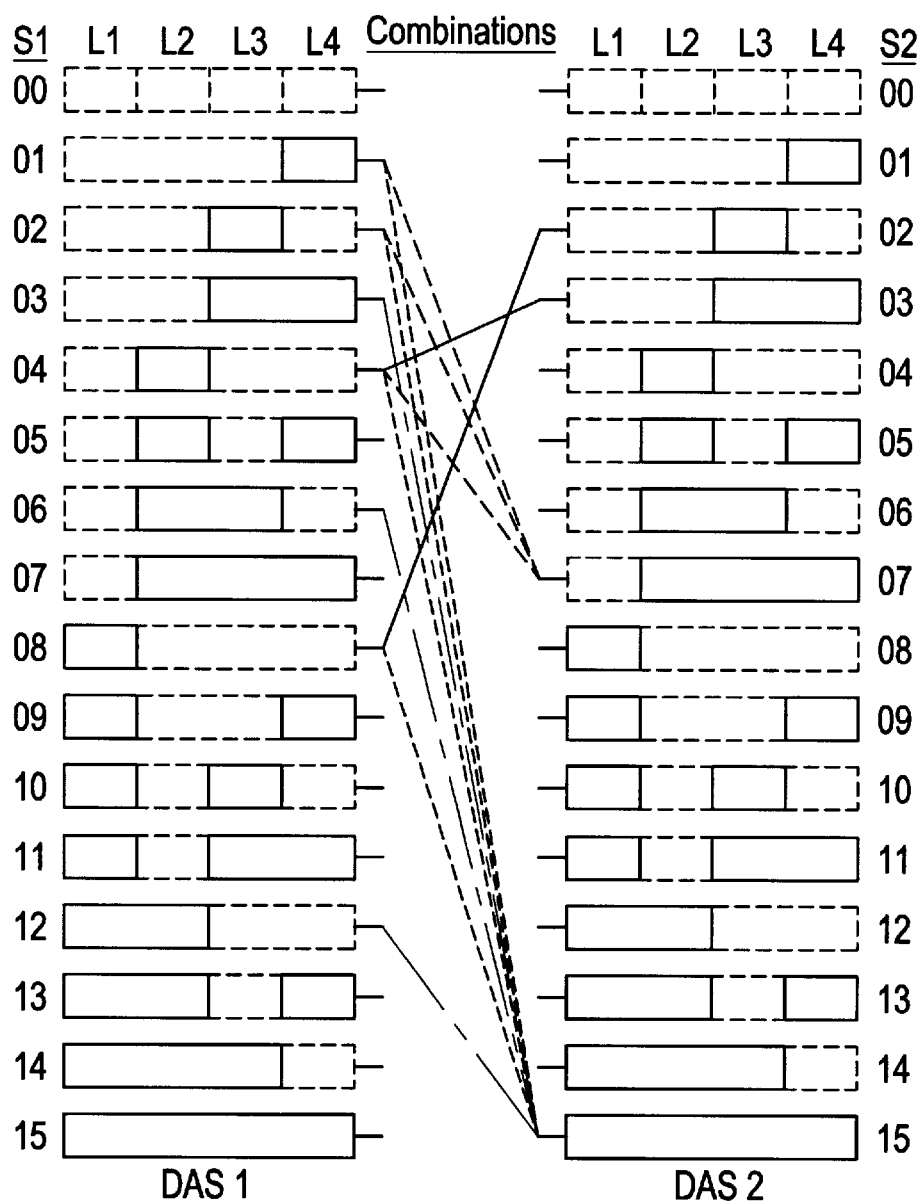
FIG. 13 is a diagram (5) for explaining data collecting patterns in the first embodiment.

FIG. 13 gives an overview of possible combinations of various data collecting patterns that can be offered by the first embodiment. As shown, there are sixteen patterns in total as the combination patterns for the projection data S1 generated by arbitrarily combining the channel detected signals of the four detector rows L1–L4, including a case in which none of the four detector rows L1–L4 is employed. The same holds for the projection data S2. Among these patterns, FIG. 9 shows four combination patterns indicated by dotted lines. FIG. 10 shows three combination patterns indicated by dot-dash lines, FIG. 11 shows three combination patterns indicated by broken lines, and FIG. 12 shows one combination pattern indicated by a solid line. Besides, other possible combination patterns can be contemplated, such as a combination pattern of (S1-08) and (S2-02), for example, as indicated by a bold line in FIG. 13. Furthermore, when useful for the medical purposes, any of several imaging patterns can be easily realized by the ON/OFF control of the switches in the signal combination section 81b. Thus, projection data having arbitrary slice widths or slice patterns can be simultaneously acquired.

Figure 14:
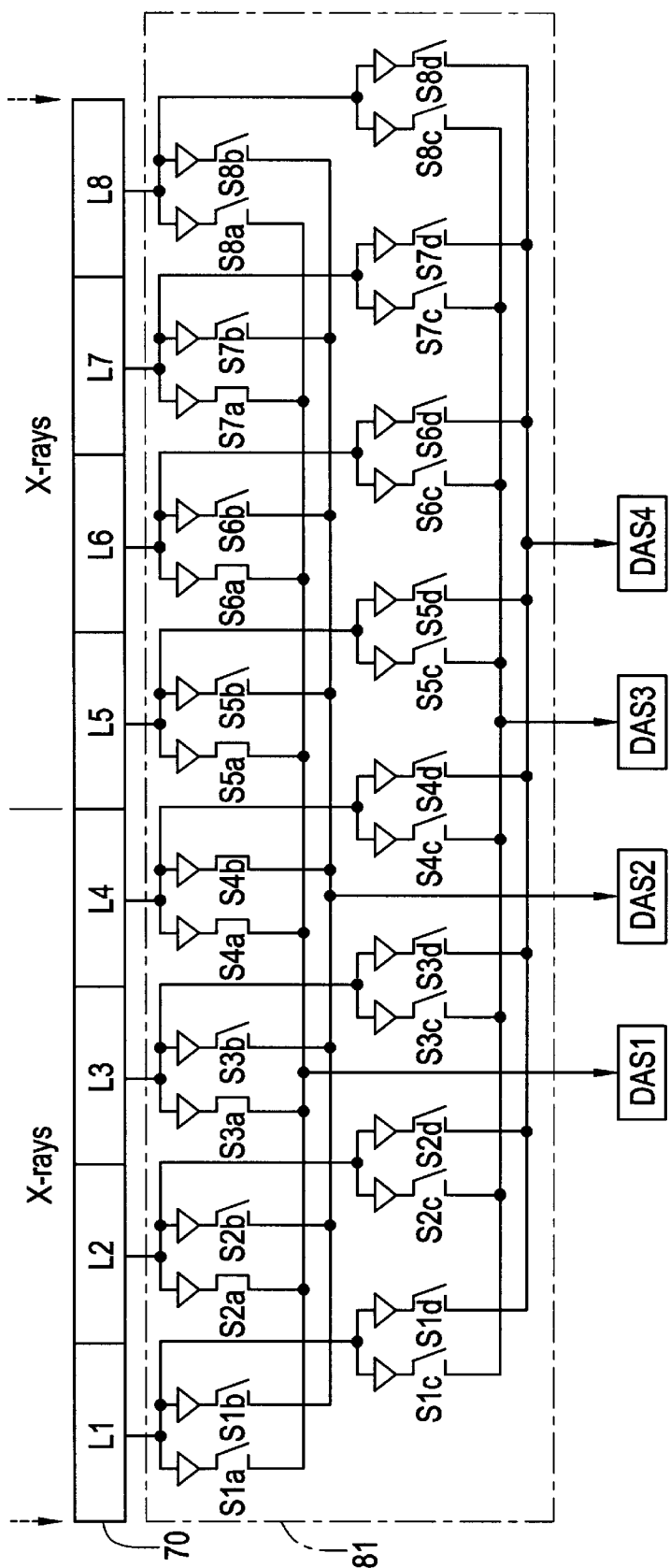
FIG. 14 is a diagram for explaining data collecting patterns in a second embodiment.
Figure 14A:
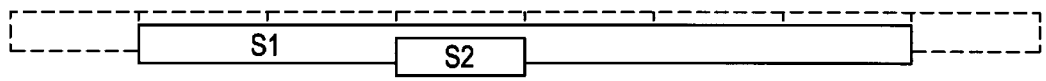
Figure 14B:
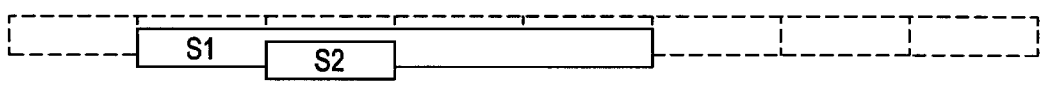
Figure 14C:
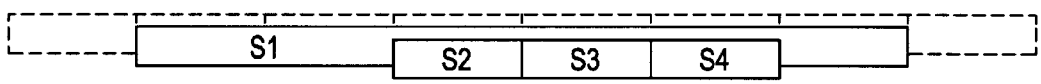
Figure 14D:
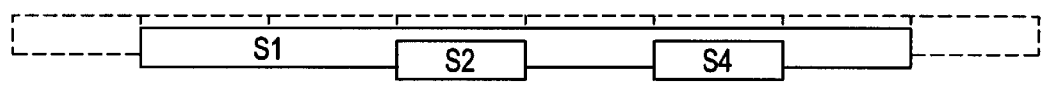

FIG. 14 is a diagram for explaining a data collecting scheme in accordance with a second embodiment, illustrating an example in which the present invention is applied to the X-ray detector 70 comprising eight detector rows L1–L8 of equal width in the subject body axis direction. The switch unit 81 in this example comprises four signal duplicating circuits and four signal combining circuits for each channel, and can simultaneously provide the four data collecting units DAS1–DAS4 with projection data having different slice widths (slice patterns).

In the inset (a), an exemplary data collecting pattern is illustrated. In this case, projection data S1 having a relatively large slice width corresponding in position to the detector rows L2–L7 is obtained, and at the same time, projection data S2 having a small slice width corresponding in position to the detector row L4 is simultaneously obtained generally in the center of the projection data S1. The inset (b) can be understood similarly to above. In the inset (c), three sets of projection data S2–S4 having a small slice width are simultaneously obtained generally in the center of the projection data S1 having the relatively large slice width. In the inset (d), from the inset (c) is eliminated the collection of the central projection data S3 having the small slice width corresponding in position to the detector row L5.

Figure 15:
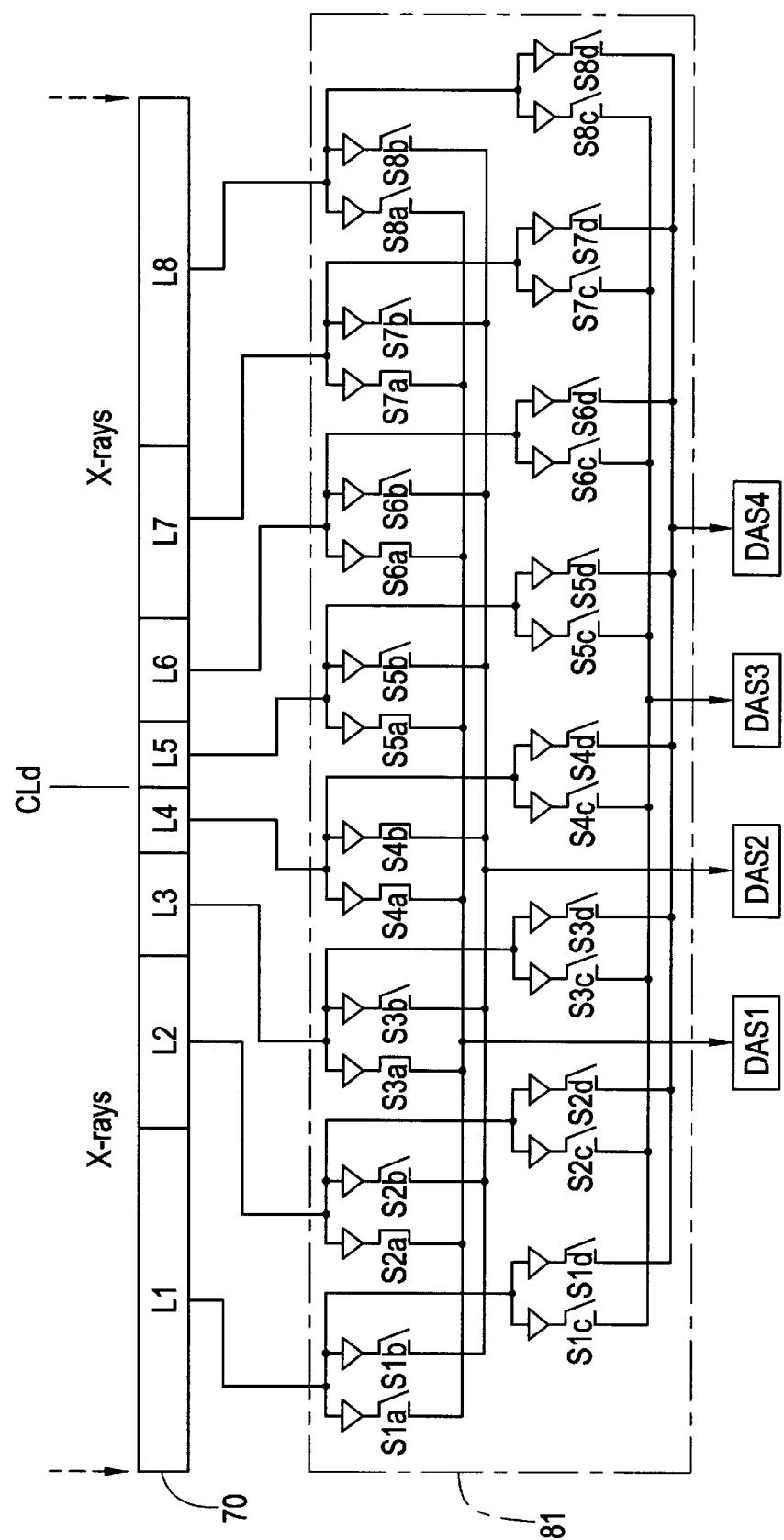
FIG. 15 is a diagram for explaining data collecting patterns in a third embodiment.
Figure 15A:
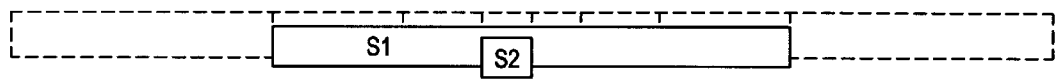
Figure 15B:
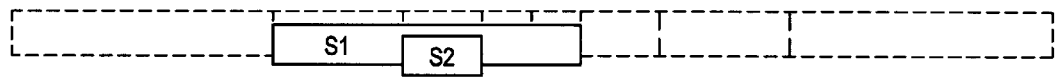
Figure 15C:
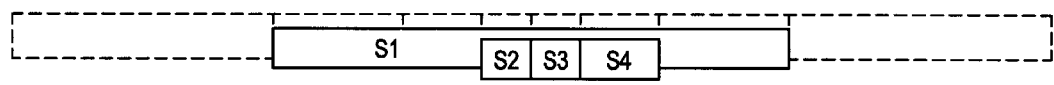
Figure 15D:
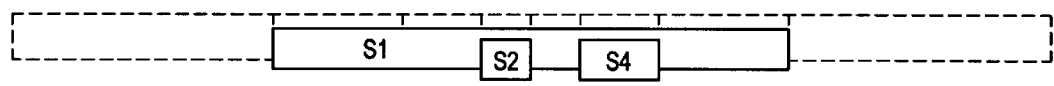

FIG. 15 is a diagram for explaining a data collecting scheme in accordance with a third embodiment, illustrating an example in which the present invention is applied to the X-ray detector 70 comprising detector rows L1–L8 having different detection widths in the subject body axis direction. Other parts of the configuration are the same as those described regarding FIG. 14. Referring to the insets (a)–(d), although the data collecting methods are the same as those described regarding FIG. 14, a very minute scan in the central portion of the detector rows and a wide range scan over the end portions of the detector rows can be simultaneously achieved because the detection widths of the detector rows L1–L8 themselves are different.

Figure 16A:
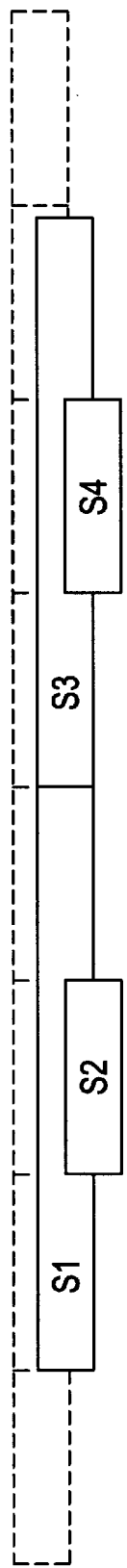
FIG. 16 is a diagram for explaining data collecting patterns in a fourth embodiment.
Figure 16B:
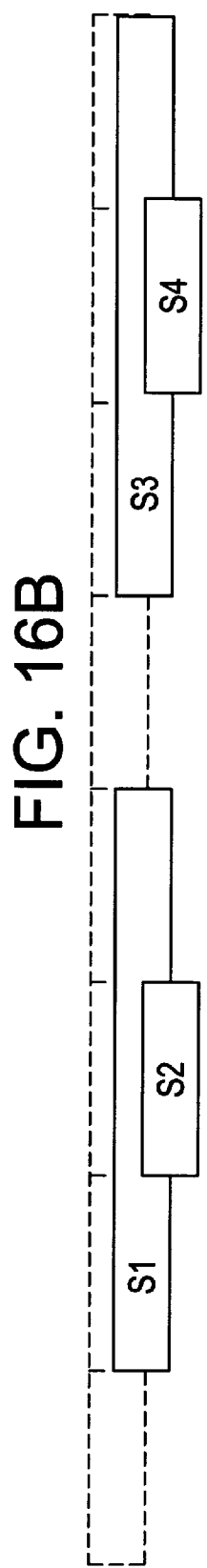

FIG. 16 is a diagram for explaining a data collecting scheme in accordance with a fourth embodiment, in which the X-ray detector 70 comprises eight detector rows L1–L8 of equal width in the subject body axis direction, and two switch units 81a and 81b as described regarding FIG. 6 are provided in parallel (corresponding to L1–L4, and L5–L8, respectively).

In the inset (a), by controlling the connections within the switch units 81a and 81b symmetrically, projection data S1–S4 symmetric with respect to the centerline CLd of the X-ray detection system can be simultaneously obtained. Moreover, in the inset (b), by controlling the connections within the switch units 81a and 81b identically, projection data S1–S4 identical (asymmetric) with respect to the centerline CLd of the X-ray detection system can be simultaneously obtained.

Figure 17:
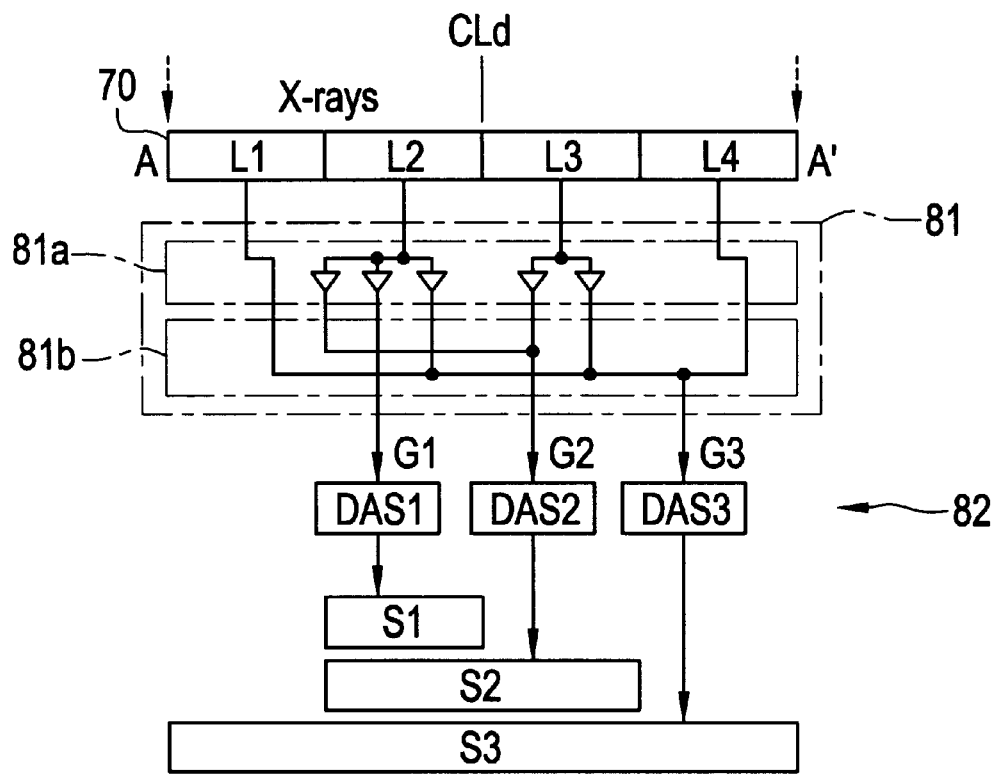
FIG. 17 is a diagram for explaining data collecting patterns in a fifth embodiment.

FIG. 17 is a diagram for explaining a data collecting scheme in accordance with a fifth embodiment, in which the X-ray detector 70 comprises four detector rows L1–L4 of equal width in the subject body axis direction, and the switch unit 81 having previously fixed signal duplication patterns and signal combination patterns is provided.

Thus, desired imaging patterns S1–S3, etc. that are symmetric/asymmetric with respect to the centerline CLd of the X-ray detector can be easily obtained in a fixed manner by the simple configuration.

FIG. 18 is a diagram for explaining a data collecting scheme in accordance with a sixth embodiment, in which several data collecting schemes are previously fixed, and a signal selecting section 81c can further select from among the fixed patterns.

Thus, a process of obtaining projection data S1 having a small detection width corresponding in position to each of the detector rows L1–L4 within projection data S2 having a large detection width, and a process of reducing the detection width for the projection data S2 to the central two rows can be easily achieved by the relatively simple configuration.

Moreover, since the signal selecting section 81c not only simply selects from among the channel combined signals of the groups G1–G6 but also operates to further combine the selected channel combined signals, more various pattern combinations can be achieved. It should be noted that the signal selecting section 81c may operate to simply select from among the channel combined signals by switching.

Although the description has been made on the examples applied to the X-ray detector 70 having four or eight rows in the preceding embodiments, the present invention can be easily applied to an X-ray detector having a different number of detector rows (16 rows, 32 rows, and the like).

Moreover, although the description has been made on several symmetric/asymmetric data collecting patterns and their combinations in the preceding embodiments, it is obvious that a variety of other data collecting patterns and their combinations can be employed.

Furthermore, although the collimator 50 has been described in the preceding embodiments as having one exemplary configuration, the collimator 50 can be implemented in any of several other configurations.

In addition, although the examples applied to the X-ray CT apparatus of the fan-beam type (generally referred to as an 'R-R type' or the like) have been described in the preceding embodiments, the present invention can be obviously applied to X-ray CT apparatuses of an 'R-S type' or the like in which a multiplicity of X-ray detector elements are circularly arranged.

Finally, although the several preferred embodiments of the present invention have been described, it is easily recognized that various changes can be made on configuration, control, processing and combination thereof of several components without departing from the concept of the present invention.

Many widely different embodiments of the invention may be configured without departing from the spirit and the scope of the present invention. It should be understood that the present invention is not limited to the specific embodiments described in the specification, except as defined in the appended claims.

What is claimed is:

1. An X-ray CT apparatus in which an X-ray tube and an X-ray detector are opposed to each other interposing a subject, in which detector a multiplicity of X-ray detector elements are linearly arranged in the channel arrangement direction to form a plurality of rows in the subject body axis direction, for reconstructing a CT tomographic image of the subject based on detected signals from the X-ray detector, comprising:
   a signal duplicating device for duplicating channel detected signals of the X-ray detector and distributing the duplicated signals to a plurality of groups;
   a signal combining device that can combine said distributed duplicated signals in each group in an arbitrary pattern across the detector rows for each channel; and
   a data collecting device for converting said channel combined signals for each group into projection data for each channel and collecting the projection data along the channel arrangement direction.

2. An X-ray CT apparatus in which an X-ray tube and an X-ray detector are opposed to each other interposing a subject, in which detector a multiplicity of X-ray detector elements are linearly arranged in the channel arrangement direction to form a plurality of rows in the subject body axis direction, for reconstructing a CT tomographic image of the subject based on detected signals from the X-ray detector, comprising:
   a signal duplicating device for duplicating channel detected signals of the X-ray detector and distributing the duplicated signals to a plurality of groups;
   a signal combining device that combines said distributed duplicated signals in each group in a predefined pattern across the detector rows for each channel; and
   a data collecting device for converting said channel combined signals for each group into projection data for each channel and collecting the projection data along the channel arrangement direction.

3. An X-ray CT apparatus in which an X-ray tube and an X-ray detector are opposed to each other interposing a subject, in which detector a multiplicity of X-ray detector elements are linearly arranged in the channel arrangement direction to form a plurality of rows in the subject body axis direction, for reconstructing a CT tomographic image of the subject based on detected signals from the X-ray detector, comprising:
   a-signal duplicating device for duplicating channel detected signals of the X-ray detector and distributing the duplicated signals to a plurality of groups;
   a signal combining device that combines said distributed duplicated signals in each group in a predefined pattern across the detector rows for each channel;
   a signal selecting device for further selecting from among said channel combined signals for the groups; and
   a data collecting device for converting said selected channel combined signals for each group into projection data for each channel and collecting the projection data along the channel arrangement direction.

4. The X-ray CT apparatus as defined in claim 1, further comprising a data processing device for combining said collected projection data for each group across the detector rows for each channel.

5. The X-ray CT apparatus as defined in claim 1, comprising an image reconstructing device for performing image reconstruction of CT tomographic images based on the data from said data collecting device.

6. The X-ray CT apparatus as defined in claim 1, wherein the X-ray detector comprises a multiplicity of X-ray detector elements linearly arranged in the channel arrangement direction to form a plurality of rows of equal detection width in the subject body axis direction.

7. The X-ray CT apparatus as defined in claim 1, wherein the X-ray detector comprises a multiplicity of X-ray detector elements linearly arranged in the channel arrangement direction to form a plurality of rows having different detection widths in the subject body axis direction.

8. The X-ray CT apparatus as defined in claim 1, wherein the signal duplicating device comprises current mirror circuits for duplicating the channel detected signal currents of the X-ray detector elements identically or in a constant ratio.

9. The X-ray CT apparatus as defined in claim 1, wherein the signal combining device comprises a plurality of switching device for individually ON/OFF controlling the duplicated signals for each group by an external control signal; and a signal combining circuit for combining output signals from said switching device for each group.

10. The X-ray CT apparatus as defined in claim 3, wherein the signal selecting device comprises a plurality of switching device for individually ON/OFF controlling the channel combined signals for each group by an external control signal; and a signal combining circuit for combining output signals from said switching device for each group.

11. The X-ray CT apparatus as defined in claim 1, comprising:
   an X-ray detector having k detector rows; and
   m ($\geq 2$) signal duplicating/combining units consisting of a set of signal duplicating device and signal combining device that can perform signal processing for the k/m detector rows so that the signal processing for the k detector rows of said X-ray detector are processed in parallel by said m signal duplicating/combining unit.

12. The X-ray CT apparatus as defined in claim 1, comprising a collimator device interposed between the X-ray tube and X-ray detector that can change the X-ray beam width in the subject body axis direction asymmetrically on both the sides of a center of said X-ray detector in the body axis direction.

13. The X-ray CT apparatus as defined in claim 12, wherein the collimator device comprises two parallel slit plates for limiting the X-ray beam width in the subject body axis direction so that slit widths formed between respective slit plates and a line assumed to lie on the center of the X-ray detector in the body axis direction can be individually changed.

14. The X-ray CT apparatus as defined in claim 1, further comprising a display device for displaying information about a scan plan, and displaying at least one of marker information of the subject slice positions and marker information of the subject slice widths on the display device corresponding to combination patterns across the detector rows specified by previously performed scan planning.

15. The X-ray CT apparatus as defined in claim 2, further comprising a data processing device for combining said collected projection data for each group across the detector rows for each channel.

16. The X-ray CT apparatus as defined in claim 3, further comprising a data processing device for combining said collected projection data for each group across the detector rows for each channel.

17. The X-ray CT apparatus as defined in claim 2, comprising an image reconstructing device for performing image reconstruction of CT tomographic images based on the data from said data collecting device.

18. The X-ray CT apparatus as defined in claim 3, comprising an image reconstructing device for performing image reconstruction of CT tomographic images based on the data from said data collecting device.

19. The X-ray CT apparatus as defined in claim 2, wherein the X-ray detector comprises a multiplicity of X-ray detector elements linearly arranged in the channel arrangement direction to form a plurality of rows of equal detection width in the subject body axis direction.

20. The X-ray CT apparatus as defined in claim 3, wherein the X-ray detector comprises a multiplicity of X-ray detector elements linearly arranged in the channel arrangement direction to form a plurality of rows of equal detection width in the subject body axis direction.

21. The X-ray CT apparatus as defined in claim 2, wherein the X-ray detector comprises a multiplicity of X-ray detector elements linearly arranged in the channel arrangement direction to form a plurality of rows having different detection widths in the subject body axis direction.

22. The X-ray CT apparatus as defined in claim 3, wherein the X-ray detector comprises a multiplicity of X-ray detector elements linearly arranged in the channel arrangement direction to form a plurality of rows having different detection widths in the subject body axis direction.

23. The X-ray CT apparatus as defined in claim 2, wherein the signal duplicating device comprises current mirror circuits for duplicating the channel detected signal currents of the X-ray detector elements identically or in a constant ratio.

24. The X-ray CT apparatus as defined in claim 3, wherein the signal duplicating device comprises current mirror circuits for duplicating the channel detected signal currents of the X-ray detector elements identically or in a constant ratio.

25. The X-ray CT apparatus as defined in claim 2, comprising a collimator device interposed between the X-ray tube and X-ray detector that can change the X-ray beam width in the subject body axis direction asymmetrically on both the sides of a center of said X-ray detector in the body axis direction.

26. The X-ray CT apparatus as defined in claim 3, comprising a collimator device interposed between the X-ray tube and X-ray detector that can change the X-ray beam width in the subject body axis direction asymmetrically on both the sides of a center of said X-ray detector in the body axis direction.

27. The X-ray CT apparatus as defined in claim 2, further comprising a display device for displaying information about a scan plan, and displaying at least one of marker information of the subject slice positions and marker information of the subject slice widths on the display device corresponding to combination patterns across the detector rows specified by previously performed scan planning.

28. The X-ray CT apparatus as defined in claim 3, further comprising a display device for displaying information about a scan plan, and displaying at least one of marker information of the subject slice positions and marker information of the subject slice widths on the display device corresponding to combination patterns across the detector rows specified by previously performed scan planning.

* * * * *